United States Patent
Ye et al.

(10) Patent No.: US 12,140,588 B2
(45) Date of Patent: Nov. 12, 2024

(54) TARGET CELL STATISTICAL METHOD, APPARATUS, AND SYSTEM

(71) Applicant: Shenzhen Mindray Bio-Medical Electronics Co., Ltd., Shenzhen (CN)

(72) Inventors: Bo Ye, Shenzhen (CN); Wei Luo, Shenzhen (CN); Yuan Xing, Shenzhen (CN); Shan Yu, Shenzhen (CN); Qiaoni Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 369 days.

(21) Appl. No.: 17/830,729

(22) Filed: Jun. 2, 2022

(65) Prior Publication Data
US 2022/0291196 A1 Sep. 15, 2022

Related U.S. Application Data

(63) Continuation of application No. PCT/CN2019/123029, filed on Dec. 4, 2019.

(51) Int. Cl.
*G01N 33/49* (2006.01)
*G01N 15/01* (2024.01)
(Continued)

(52) U.S. Cl.
CPC ............ *G01N 33/49* (2013.01); *G06T 7/0014* (2013.01); *G06T 7/90* (2017.01); *G06V 20/69* (2022.01);
(Continued)

(58) Field of Classification Search
CPC ....... G06T 7/0012; G06T 7/0014; G06T 7/90; G06T 2207/20081; G06T 2207/30004; G06T 2207/30024; G06V 20/69; G06V 20/693; G06V 20/695; G06V 20/698; G01N 33/49; G01N 33/491; G01N 2015/012;
(Continued)

(56) References Cited

U.S. PATENT DOCUMENTS

| 10,169,861 B2 * | 1/2019 | Ozaki | .................... G06T 7/0012 |
| 2010/0054575 A1 * | 3/2010 | Zhou | .................. G01N 15/1459 382/134 |

(Continued)

FOREIGN PATENT DOCUMENTS

| CN | 1945326 A | 4/2007 |
| CN | 103345654 A | 10/2013 |

(Continued)

*Primary Examiner* — Scott A Rogers
(74) *Attorney, Agent, or Firm* — Kory D. Christensen

(57) ABSTRACT

A target cell statistical method, apparatus and system are provided. A cell image of a blood specimen is acquired by a cell image analysis apparatus. The blood specimen is derived from a blood sample to be tested. A number of target cells and a number of reference cells in the cell image are automatically identified by the cell image analysis apparatus. A number of reference cells in the blood sample to be tested is acquired by the cell image analysis apparatus, and a number of target cells in the blood sample to be tested is calculated by the cell image analysis apparatus, based on the number of target cells and the number of reference cells in the cell image and the number of reference cells in the blood sample to be tested.

20 Claims, 20 Drawing Sheets

A cell image of a blood specimen is acquired by a cell image analysis apparatus, the blood specimen is derived from a blood sample to be tested — 501

A number of target cells and a number of reference cells in the cell image are automatically identified by the cell image analysis apparatus — 502

A number of reference cells in the blood sample to be tested is acquired, and a number of target cells in the blood sample to be tested is calculated based on the number of target cells and the number of reference cells in the cell image and the number of reference cells in the blood sample to be tested, by the cell image analysis apparatus — 503

(51) Int. Cl.
   *G01N 15/14* (2024.01)
   *G06T 7/00* (2017.01)
   *G06T 7/90* (2017.01)
   *G06V 20/69* (2022.01)

(52) U.S. Cl.
   CPC . *G01N 2015/012* (2024.01); *G01N 2015/016* (2024.01); *G01N 2015/1472* (2013.01); *G06T 2207/20081* (2013.01); *G06T 2207/30024* (2013.01)

(58) Field of Classification Search
   CPC ....... G01N 2015/016; G01N 2015/018; G01N 2015/1472
   See application file for complete search history.

(56) References Cited

U.S. PATENT DOCUMENTS

2022/0334100 A1* 10/2022 Qi ..................... G01N 15/1431
2022/0341912 A1* 10/2022 Viallat ................. G06T 7/0014

FOREIGN PATENT DOCUMENTS

| CN | 107478818 A | 12/2017 |
| CN | 109507406 A | 3/2019 |
| JP | 4690165 B2 * | 6/2011 |

\* cited by examiner

TARGET CELL STATISTICAL METHOD, APPARATUS, AND SYSTEM

CROSS-REFERENCE TO RELATED APPLICATION

The present application is a U.S. continuation application of International Application No. PCT/CN2019/123029, filed on Dec. 4, 2019, the contents of which are hereby incorporated by reference in its entirety.

BACKGROUND

Blood platelet (PLT) is the smallest one of blood cells, with an average diameter of only 2 to 4 microns. Blood platelet counting refers to the number of blood platelets contained in a unit volume of blood. The number of blood platelets in a normal person's blood is maintained at a certain level. The number of blood platelets may be decreased or increased due to certain diseases. Blood platelet counting is helpful in the clinical diagnosis and differential diagnosis of hemostasis and thrombotic diseases.

Currently, blood analyzers can count blood platelets based on their small size. For normal samples, the blood analyzer can accurately count blood platelets. However, for abnormal samples (for example, increased cell debris, blood platelet aggregation, etc.), the blood platelet counting results of the blood analyzer have a large deviation. In this case, the inspector needs to re-examine under the microscope to confirm the blood platelet counting value.

The blood platelet counting method of manual re-examination under the microscope generally adopts the filling cell counting method. In the filling cell counting method, the pretreated blood is injected into the counting cell to be counted, and the number of blood platelets in the counting cell is counted with a high-power microscope. Since the volume of the counting cell is determined, the number of blood platelets per liter of blood can be calculated. However, the filling cell counting method requires the counting personnel to observe and count under the microscope for a long time, which is prone to visual fatigue and low counting efficiency.

SUMMARY

The present disclosure relates to the field of medical instruments, and in particular, to a target cell statistical method, apparatus, system and storage medium.

The embodiments of the present disclosure provide a target cell statistical method, apparatus, system and storage medium, which can improve blood platelet counting efficiency.

In a first aspect of the embodiments of the present disclosure, a target cell statistical method is provided. The method includes the following operations.

A cell image of a blood specimen is acquired by a cell image analysis apparatus. The blood specimen is derived from the blood sample to be tested.

The number of target cells and the number of reference cells in the cell image are automatically identified by the cell image analysis apparatus.

The number of reference cells in the blood sample to be tested is acquired, and the number of target cells in the blood sample to be calculated based on the number of target cells and the number of reference cells in the cell image and the number of reference cells in the blood sample to be tested, by the cell image analysis apparatus.

In a second aspect of the embodiments of the present disclosure, a cell image analysis apparatus is provided. The cell image analysis apparatus includes an imaging apparatus, a specimen moving apparatus and a processor.

The imaging apparatus includes a camera and a lens group, and is configured to photograph a cell image of a blood specimen derived from a blood sample to be tested.

The specimen moving apparatus is configured to move the blood specimen relative to the imaging apparatus so that the imaging apparatus photographs a cell image of a specific region of the blood specimen.

The processor is configured to acquire a cell image of the blood specimen derived from the blood sample to be tested, and is further configured to automatically identify the number of target cells and the number of reference cells in the cell image; and is further configured to acquire the number of reference cells in the blood sample to be tested.

The processor is further configured to calculate the number of target cells in the blood sample to be tested based on the number of target cells and the number of reference cells in the cell image, and the number of reference cells in the blood sample to be tested.

In a third aspect of the embodiments of the present disclosure, a specimen analysis system is provided. The specimen analysis system includes a cell image analysis apparatus and a blood analyzer. The cell image analysis apparatus includes an imaging apparatus, a specimen moving apparatus and a processor.

The imaging apparatus includes a camera and a lens group, and is configured to photograph a cell image of a blood specimen derived from the blood sample to be tested.

The specimen moving apparatus is configured to move the blood specimen relative to the imaging apparatus so that the imaging apparatus photographs a cell image of a specific region of the blood specimen.

The blood analyzer is configured to detect the number of reference cells in the blood sample to be tested.

The processor is configured to acquire a cell image of the blood specimen, and automatically identify the number of target cells and the number of reference cells in the cell image; and is further configured to acquire the number of reference cells in the blood sample to be tested from the blood analyzer; is further configured to calculate the number of target cells in the blood sample to be tested based on the number of target cells and the number of reference cells in the cell image, and the number of reference cells in the blood sample to be tested.

In a fourth aspect of the embodiments of the present disclosure, a cell image analysis apparatus is provided. The cell image analysis apparatus includes a processor and a memory. The memory is configured to store a computer program that includes program instructions. The processor is configured to invoke the program instructions to execute the step instructions in the first aspect of the embodiments of the present disclosure.

In a fifth aspect of the embodiments of the present disclosure, a computer-readable storage medium is provided. The computer-readable storage medium stores a computer program for electronic data exchange. The computer program causes the computer to execute some or all of the steps described in the first aspect of the embodiments of the present application.

In a sixth aspect of the embodiments of the present disclosure, a computer program product is provided. The computer program product includes a non-transitory computer-readable storage medium storing a computer program. The computer program is operable to cause the computer to perform some or all of the steps as described in the first aspect of the embodiments of the present disclosure. The computer program product may be a software installation package.

In the embodiments of the present disclosure, by the cell image analysis apparatus, the number of target cells and the number of reference cells in the cell image of the blood specimen may be automatically identified, and the number of target cells in the blood sample to be tested is calculated based on the number of target cells and the number of reference cells in the cell image, and the number of reference cells in the blood sample to be tested. The number of target cells in the blood sample to be tested can be accurately calculated. Compared with the manual counting method, the inspector does not need to count the target cells under the microscope for a long time, the counting efficiency of the target cells is improved, while manual errors are avoided.

BRIEF DESCRIPTION OF THE DRAWINGS

In order to more clearly illustrate the embodiments of the present disclosure or the technical solutions in the prior art, the accompanying drawings required for the description of the embodiments or the prior art will be briefly introduced below. It is apparent that the drawings in the following description are only some embodiments of the present disclosure. For those of ordinary skill in the art, other accompanying drawings can also be obtained based on these accompanying drawings without any creative effort.

DETAILED DESCRIPTION

The technical solutions in the embodiments of the present disclosure will be clearly and fully described below with reference to the drawings in the embodiments of the present disclosure. It is apparent that the described embodiments are only some embodiments of the present disclosure, but not all of the embodiments. Based on the embodiments in the present disclosure, all other embodiments obtained by those of ordinary skill in the art without creative efforts shall fall within the protection scope of the present disclosure.

The terms "first", "second" and the like in the specification, the claims and the above drawings of the present disclosure are used to distinguish different objects, rather than to describe a specific order. Furthermore, the terms "including", "having" and any variations thereof refer to non-exclusive inclusion. For example, a process, method, system, product or device including a series of steps or units is not limited to the listed steps or units, but optionally may include unlisted steps or units, or optionally may further include other steps or units inherent to the process, method, product or device.

Reference to an "embodiment" in the present disclosure means that a particular feature, structure, or characteristic described with reference to the embodiment can be included in at least one embodiment of the present disclosure. The appearances of the term in various places in the specification are not necessarily all referring to the same embodiment, nor a separate or alternative embodiment that is mutually exclusive of other embodiments. It is explicitly and implicitly understood by those skilled in the art that the embodiments described in the present disclosure may be combined with other embodiments.

The embodiments of the present disclosure will be described in detail below.

Figure 1A:
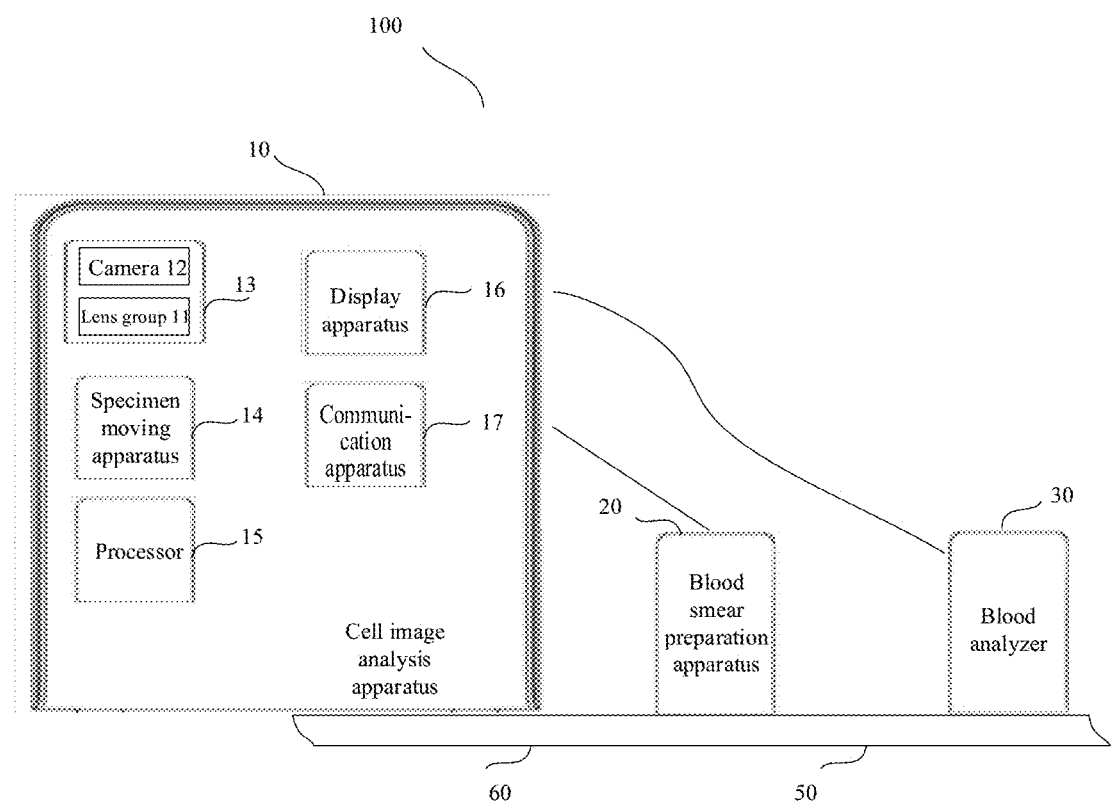
FIG. 1A illustrates a schematic structure diagram of a specimen analysis system disclosed in an embodiment of the present disclosure.

With reference to FIG. 1A, FIG. 1A illustrates a schematic structure diagram of a specimen analysis system disclosed in an embodiment of the present disclosure. As illustrated in FIG. 1A, the specimen analysis system 100 may include a cell image analysis apparatus 10 and a blood analyzer 30. The cell image analysis apparatus 10 includes an imaging apparatus 13, a specimen moving apparatus 14 and a processor 15.

The imaging apparatus 13 includes a camera 12 and a lens group 11. The imaging apparatus 13 is configured to photograph a cell image of a blood specimen derived from the blood sample to be tested.

The specimen moving apparatus 14 is configured to move the blood specimen relative to the imaging apparatus 13, so that the imaging apparatus 13 photographs a cell image of a specific region of the blood specimen.

The blood analyzer 30 is configured to detect the number of reference cells in the blood sample to be tested.

The processor 15 is configured to acquire a cell image of the blood specimen. The processor is further configured to automatically identify the number of target cells and the number of reference cells in the cell image. The processor is further configured to acquire the number of reference cells in the blood sample to be tested from the blood analyzer 30. The processor is further configured to calculate the number of target cells in the blood sample to be tested based on the number of target cells and the number of reference cells in the cell image, and the number of reference cells in the blood sample to be tested.

Optionally, the number of reference cells in the blood sample to be tested acquired by the processor may be the concentration of reference cells in the blood sample to be tested.

Figure 3:
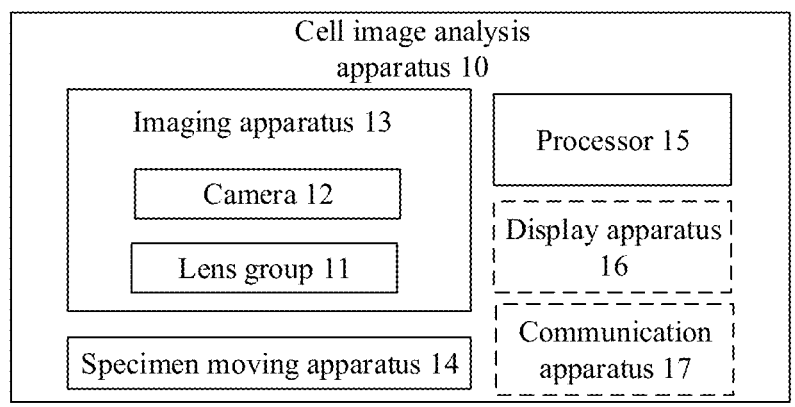
FIG. 3 illustrates a schematic structure diagram of a cell image analysis apparatus disclosed in an embodiment of the present disclosure.

Optionally, as illustrated in FIG. 1A, the cell image analysis apparatus 10 may further include a display apparatus 16. The display apparatus 16 is configured to at least display the number of target cells in the blood sample to be tested. For the specific structure of the cell image analysis apparatus 10, reference may also be made to FIG. 3.

The display apparatus 16 may include a liquid crystal display, a light emitting diode (LED) display, an organic light emitting diode (OLED) display, and the like.

Optionally, that the processor 15 acquires a cell image of the blood specimen, is specifically as follows. The processor 15 acquires an input cell image of the blood specimen.

In the embodiments of the present disclosure, the processor 15 may receive cell images of blood specimens sent by other devices. The other devices may store cell images of blood specimens beforehand. The other devices may also be devices with a photographing function. For example, the processor 15 may establish a communication connection with the other device with the photographing function. After the cell images of blood specimens are photographed by other devices with the photographing function, the processor 15 acquires cell images of blood specimens input by the other devices with the photographing function.

Optionally, as illustrated in FIG. 1A, the cell analysis apparatus 10 further includes a communication apparatus 17. The communication apparatus 17 may include at least one of a communication interface, or an input/output (I/O) interface. For the specific structure of the cell image analysis apparatus 10, reference can also be made to FIG. 3.

That the processor 15 is configured to acquire the number of reference cells in the blood sample to be tested from the blood analyzer 30, includes: the processor 15 controls the communication apparatus 17 to automatically acquire the number of reference cells in the blood sample to be tested from the blood analyzer 30.

The processor 15 may also receive cell images of the blood specimens input by other devices or users through an I/O interface (for example, a USB interface). The processor 15 may also receive the cell image of the blood specimen sent by a server through the communication interface.

In the case where the cell image analysis apparatus 10 does not have a photographing function, or the photographing apparatus of the cell image analysis apparatus 10 is damaged and cannot work, an input cell image of the blood specimen can be acquired.

The imaging device 13 is configured to capture a cell image of the blood specimen through the camera 12 and the lens group 11. The blood specimen is derived from the blood sample to be tested.

That the processor 15 acquires the cell image of the blood specimen, is specifically as follows. The processor 15 acquires the cell image of the blood specimen from imaging apparatus 13.

In some embodiments, the cell image analysis apparatus may store cell images, and the user may select a cell image from the stored cell images. The processor receives the user's selection instruction, and then acquires the cell image of the blood specimen.

In the embodiments of the present disclosure, the cell image analysis apparatus, which may also be referred to as a slide reader, a cell image analysis system, or a cell image digital analysis system, can automatically photograph and analyze the blood specimen. It can also estimate the number of blood cells in the blood specimen. The cell image analysis apparatus may estimate the number of blood cells in the cell image of the blood specimen by an image processing algorithm. Blood cells can include red blood cells, white blood cells, and blood platelets.

In the embodiments of the present disclosure, the target cells and reference cells are different blood cells. For example, when the target cells are blood platelets, the reference cells may include one of red blood cells, white blood cells, or a combination of red blood cells and white blood cells. When the target cells are red blood cells, the reference cells may include one of white blood cells, blood platelets, or a combination of white blood cells and blood platelets. When the target cells are white blood cells, the reference cells may include one of red blood cells, blood platelets, or a combination of red blood cells and blood platelets.

In the embodiments of the present disclosure, the blood sample to be tested is a blood sample that needs to count target cells. The blood specimen is derived from the blood sample to be tested. Specifically, the blood specimen can be extracted from the blood sample to be tested. For example, a blood specimen may be loaded in a blood smear.

The blood smear may be prepared automatically by the blood smear preparation apparatus, or may be prepared manually, which is not limited in the embodiments of the present disclosure.

When a blood smear is manually prepared, the materials required for the preparation of blood smear include pipettes, glass slides, push slides (for example, double concave slides), etc. The preparation process of the blood smear can specifically include the following steps.

(1) A certain volume of blood sample is taken from the blood sample to be tested by using a pipette, and part of the blood sample (for example, a drop of blood sample) in the pipette is placed on one end of a glass slide.

(2) The glass slide is fixed with one hand, and the push slide is placed on one end of the glass slide obliquely with the other hand to contact the blood drop on the glass slide. The push slide is moved back from the front of the blood drop, keeping in contact with the blood drop, so that the blood drop spreads out into a line along the end of the glass slide.

(3) The push slide is moved forward by maintaining a certain angle (such as 30-45 degrees) with the glass slide, and then a thin layer of blood film can be formed on the glass slide, that is, a blood film is coated.

(4) When the blood film is completely dried in the air, a few drops of staining solution are dropped on the blood film. After fixing for a period of time (for example, 0.5-1.0 minute), the same amount or slightly more buffer solution is added dropwise, and the buffer solution is mixed with the staining solution to stain the blood film for a period of time (for example, 5-10 minutes).

(5) The staining solution is rinsed with distilled water, and after drying naturally, the prepared blood smear will be obtained.

After the prepared blood smear is obtained, the prepared blood smear can be placed under the lens group 11 for microscopic examination. The photographing apparatus (for example, a camera) 12 in the cell image analysis apparatus 10 can photograph the prepared blood smear, to obtain a cell image of the blood specimen in the blood smear.

Optionally, as illustrated in FIG. 1A, the specimen analysis system 100 further includes a blood smear preparation apparatus 20. The blood smear preparation apparatus 20 is configured to prepare the smear of the blood sample to be tested as the blood specimen to be photographed.

Figure 2:
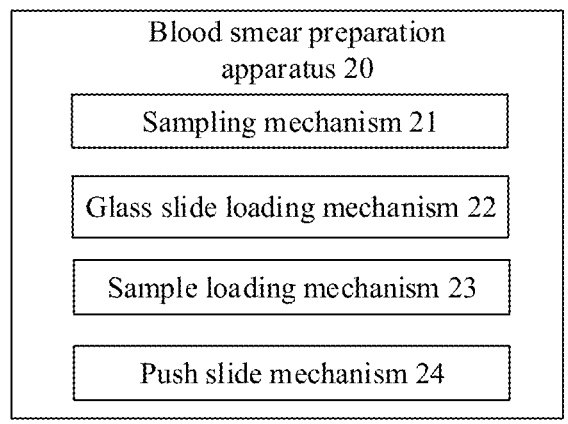
FIG. 2 illustrates a schematic structure diagram of a blood smear preparation apparatus disclosed in an embodiment of the present disclosure.

When the blood smear preparation apparatus 20 automatically prepares the blood smear, the blood smear preparation apparatus needs to be used. The structure of the blood smear preparation apparatus is shown in FIG. 2. The blood smear preparation apparatus 20 may include a sampling mechanism 21, a glass slide loading mechanism 22, a sample loading mechanism 23 and a push slide mechanism 24.

The sampling mechanism 21 is configured to suck a blood specimen from the blood sample to be tested.

The glass slide loading mechanism 22 is configured to move a blank glass slide to the operation position.

The sample loading mechanism 23 is configured to load the blood specimen onto the blank glass slide.

The push slide mechanism 24 is configured to smoothly spread the blood specimen on the blank glass slide to prepare a blood smear.

The sampling mechanism 21 can suck a blood specimen from a blood sample to be tested in a vessel (for example, a test tube, a cup, etc. containing blood). The sampling mechanism 21 may include a pipette for sucking liquid, a pipette control apparatus (for example, an automatic control apparatus for squeezing the pipette) for controlling the pipette to suck the liquid, a movable robotic arm. The pipette controlling apparatus is fixedly arranged on the robotic arm, and the pipette may be fixedly arranged on the robotic arm at a position where the pipette control apparatus can squeeze the pipette. The glass slide loading mechanism 22 may include a gripping apparatus (for example, a robotic arm) for gripping the blank glass slide. The sample loading mechanism 23 may include the pipette, the pipette control apparatus, and the movable robotic arm in the sampling mechanism 21. The push slide mechanism 24 may include a push slide control mechanism, a glass slide fixing mechanism, and the gripping apparatus in the glass slide loading mechanism 22.

The blood smear preparation apparatus 20 can perform an automatic blood smear preparation procedure. It controls the gripping apparatus of the glass slide loading mechanism 22 to grip the blank glass slide from the position where the blank glass slide is placed, and moves the gripped blank glass slide to the operation position. The blood smear preparation apparatus 20 controls the robotic arm of the sampling mechanism 21 to move to the position where the vessel containing the blood sample to be tested is placed, and controls the robotic arm to insert the pipette tip into the blood sample to be tested in the vessel. The blood smear preparation apparatus 20 controls the pipette control apparatus of the sampling mechanism 21 to squeeze the gas in the pipette, thereby controlling the pipette to draw a certain amount of blood specimen from the vessel. The blood smear preparation apparatus 20 controls the robotic arm to move to the blank glass slide at the operation position, and controls the pipette control apparatus of the sampling mechanism 21 to squeeze the gas in the pipette, thereby controlling the blood specimen in the pipette to flow out of the pipette onto the blank glass slide. The blood smear preparation apparatus 20 controls the gripping apparatus to grip the push slide, and place the push slide obliquely at one end of the blank glass slide to contact the blood specimen on the blank glass slide. The blood smear preparation apparatus 20 controls the gripping apparatus to move the push slide from one end of the blank glass slide to the other end to form a blood film on the blank glass slide. After the blood film is completely dried in the air, the blood smear preparation apparatus 20 controls the staining solution pipette to suck the staining solution and drop onto the blood film. After fixing for a period of time (for example, 0.5-1.0 minute), the blood smear preparation apparatus 20 controls the buffer solution pipette to suck the buffer solution. After the buffer solution is mixed with the staining solution homogenously for staining for a period of time (for example, 5-10 minutes), the blood smear preparation apparatus 20 controls the distilled water pipette to suck the distilled water to wash the staining solution on the glass slide, and after drying naturally, the prepared blood smear can be obtained. The blood smear can be automatically prepared and the blood smear preparation efficiency can be improved by the blood smear preparation apparatus in the embodiments of the present disclosure.

Optionally, that the processor 15 acquires the cell image of the blood specimen includes the processor 15 acquires at least two cell images of the (same) blood specimen (which may be acquired simultaneously or sequentially). Subsequently, when the processor automatically identifies the number of target cells and the number of reference cells in the cell image, it may automatically identify (simultaneously or sequentially) the number of target cells and the number of reference cells in the at least two cell images. It may superimpose the number of target cells in each of the at least two cell images to obtain the number of target cells in the at least two cell images, and it may superimpose the number of reference cells in each of the at least two cell images to obtain the number of reference cells in the at least two cell images. Alternatively, the at least two cell images may be spliced into one cell image before being identified. That is, the processor automatically identifies the number of target cells and reference cells in the spliced cell image.

The regions included in the at least two pictures may overlap or not, which is not limited in the embodiments of the present disclosure. When they overlap, the overlapping part needs to be removed during splicing to avoid repeated counting.

Optionally, the blood specimen is prepared into a blood smear, and that the processor 15 acquires a cell image of the blood specimen photographed by the imaging apparatus 13 is specifically as follows.

The processor 15 acquires a cell image of the specific region of the blood smear photographed by the imaging apparatus 13. The specific region includes at least one of a body-tail junction region, a body region, an edge region at either side, or a tail region of the blood smear.

The body-tail junction region of the blood smear is a better region for observing the morphology of blood cells. The specific region may also be a cell monolayer region of the blood smear. When the imaging apparatus 13 photographs the prepared blood smear, it may automatically photograph a cell image of a certain area of the specific region of the blood smear, for example, the monolayer region of the reference cells of the blood smear, and ensure that the reference cells included in the photographed area reach the preset number threshold. The greater the number of reference cells in the cell image, the greater the reference significance of the reference cells, and the higher the accuracy of the number of target cells in the blood sample to be tested can be obtained by subsequent calculation. The preset number threshold may be set in advance and stored in a memory (for example, a nonvolatile memory) of the cell image analysis apparatus 10. For example, the preset number threshold may be 1000.

Optionally, the blood specimen is prepared into a blood smear. That the processor 15 acquires a cell image of the blood specimen photographed by the imaging apparatus 13 is specifically as follows.

The processor 15 acquires at least two cell pictures of the specific region of the blood smear photographed by the imaging apparatus 13. The specific region includes at least one of a body-tail junction region, a body region, an edge region at either side, or a tail region of the blood smear.

The processor 15 combines the above at least two cell pictures into a cell image, and the cell image includes the at least two cell pictures or the cell image is formed by splicing the at least two cell pictures.

In the embodiments of the present disclosure, when the number of reference cells included in the cell picture of a specific region of the blood smear photographed by the imaging apparatus 13 is small, the imaging apparatus 13 may be controlled to photograph at least two cell pictures of the specific region of the blood smear, and the at least two cell pictures are combined into a cell image. In this way, it can be ensured that the number of reference cells included in the cell image can reach a preset number threshold, thereby improving the accuracy of the number of target cells in the blood sample to be tested obtained by subsequent calculation.

Combining the at least two cell pictures into a cell image may include the at least two cell pictures are considered as a whole, that is, as the cell image, and the cell image includes the at least two cell pictures, the at least two cell pictures are not subjected to any processing. When the cell image analysis apparatus automatically identifies the number of target cells and the number of reference cells in the cell image subsequently, it may automatically identify the number of target cells and the number of reference cells in the at least two cell pictures respectively, and it may superimpose the numbers of target cells in the at least two cell pictures to obtain the number of target cells in the cell image, and it may superimpose the numbers of reference cells in the at least two cell pictures to obtain the number of reference cells in the cell image. Combining the at least two cell pictures into a cell image may further include the at least two cell pictures are spliced into one cell image.

The regions included in the at least two pictures may overlap or not, which is not limited in the embodiments of the present disclosure. When they overlap, the overlapping part needs to be removed during splicing to avoid repeated counting.

Optionally, the at least two pictures (which may be directly used as the cell image) acquired may also be cell images of a blood specimen input by other devices or users and received by the processor, as described above, which is not limited herein.

Optionally, after the processor 15 is configured to automatically identify the number of target cells and the number of reference cells in the cell image, the processor 15 is further configured as follows.

The processor 15 is configured to perform the step of acquiring the number of reference cells in the blood sample to be tested, and calculating the number of target cells in the blood sample to be tested based on the number of target cells and the number of reference cells in the cell image and the number of reference cells in the blood sample to be tested, in the case where the number of reference cells is greater than or equal to a first threshold.

In the embodiments of the present disclosure, when the sum of the numbers of reference cells in the at least two cell images of the blood specimen acquired by the processor is greater than or equal to the first threshold, or the number of reference cells in the cell image of a specific region of the blood smear photographed by the imaging apparatus 13 is greater than or equal to the first threshold, or the number of reference cells in the cell image formed by combining at least two cell pictures of a specific region of the blood smear photographed by the imaging apparatus 13 is greater than or equal to the first threshold, it is considered that the number of reference cells included in the cell image meets the accuracy requirements for subsequent calculations, and the next step may be performed.

Optionally, after the processor 15 is configured to automatically identify the number of target cells and the number of reference cells in the cell image, the processor 15 is further configured as follows.

The processor 15 is configured to continue to perform the step of acquiring a cell image of a blood specimen, in the case where the number of reference cells is less than the first threshold.

In the embodiments of the present disclosure, when the number of reference cells is less than the first threshold, it indicates that the number of reference cells in the current cell image cannot meet the accuracy requirements of subsequent calculations, and then cell images are further acquired to be analyzed.

The first threshold may be set in advance and stored in a memory (for example, a nonvolatile memory) of the cell image analysis apparatus 10. For example, the first threshold may be 1000. The first threshold may be the same as or different from the preset number threshold, which is not limited in the embodiments of the present disclosure.

Optionally, after the processor 15 is configured to automatically identify the number of target cells and the number of reference cells in the cell image, the processor 15 is further configured as follows.

The processor 15 is configured to determine whether the sum of the numbers of reference cells in all cell images of the blood specimen acquired in history is greater than or equal to a second threshold.

That the processor 15 acquires the number of reference cells in the blood sample to be tested, and calculates the number of target cells in the blood sample to be tested based on the number of target cells and the number of reference cells in the cell image and the number of reference cells in the blood sample to be tested, is specifically as follows.

The processor 15 acquires the number of reference cells in the blood sample to be tested, and calculates the number of target cells in the blood sample to be tested based on the sum of the numbers of reference cells in all cell images of the blood specimen, the sum of the numbers of target cells in all cell images of the blood specimen, and the number of reference cells in the blood sample to be tested, in the case where the sum of the numbers of reference cells in all cell images of the blood specimen acquired in history is greater than or equal to the second threshold.

Optionally, after the processor 15 is configured to determine whether the sum of the numbers of the reference cell of all the cell images of the blood specimen acquired in history is greater than or equal to the second threshold, the processor 15 is further configured as follows.

The processor 15 is configured to continue to perform the step of acquiring the cell image of the blood specimen, in the case where the sum of the numbers of the reference cells of all the cell images of the blood specimen acquired in history is less than the second threshold.

In the embodiments of the present disclosure, for the same blood specimen, after the processor 15 analyzes the cell image of the blood specimen each time, when it is determined that the sum of the numbers of the reference cells of all the cell images of the blood specimen is less than the second threshold, the processor 15 may continue to acquire a cell image of the blood specimen; when it is determined that the sum of the numbers of the reference cells in all cell images of the blood specimen is greater than the second threshold, the processor 15 may acquire the number of reference cells in the blood sample to be tested, and calculate the number of target cells in the blood sample to be tested based on the sum of the numbers of reference cells in all cell images of the blood specimen, the sum of the numbers of target cells in all cell images of the blood specimen, and the number of reference cells in the blood sample to be tested.

The blood analyzer is further configured to detect the number of target cells in the blood sample to be tested, independent of the cell image analysis apparatus.

The system may further comprise a display apparatus, and the display apparatus is configured to display at least one of the number of target cells in the blood sample to be tested calculated by the cell image analysis apparatus, or the number of target cells in the blood sample to be tested detected by the blood analyzer.

The display apparatus is configured to display the number of target cells in the blood sample to be tested detected by the blood analyzer, when the number of reference cells in all cell images of the blood specimen acquired by the processor of the cell image analysis apparatus is less than the second threshold. As described in the above, the greater the number of reference cells in the cell image, the greater the reference significance of the reference cells, and the higher the accuracy of the number of target cells in the blood sample to be tested can be obtained by subsequent calculation. If the processor of the cell image analysis apparatus acquires the number of reference cells from the cell image of the blood specimen which is greater than or equal to the second threshold, the accuracy of the number of target cells in the blood sample calculated will be high. If the number of reference cells in all cell images of the blood specimen acquired by the processor of the cell image analysis apparatus is less than the second threshold, the display apparatus may display the number of target cells in the blood sample to be tested detected by the blood analyzer.

As example is shown as follows. The second threshold is set as 1000. The processor 15 analyzes for the first time the first cell image of the blood specimen photographed. The number of reference cells in the first cell image obtained is 100. Since the number of reference cells in the first cell image is less than the second threshold, the processor 15 analyzes for the second time the second cell image of the blood specimen photographed. The number of reference cells in the second cell image obtained is 200. Since the sum (i.e., 300) of the number of reference cells in the first cell image and the number of reference cells in the second cell image is still less than the second threshold, the processor 15 analyzes for the third time the third cell image of the blood specimen photographed. The number of reference cells in the third cell image obtained is 300. Since the sum (i.e., 600) of the number of reference cells in the first cell image, the number of reference cells in the second cell image, and the number of reference cells in the third cell image is still less than the second threshold, the processor 15 analyzes for the fourth time the fourth cell image of the blood specimen photographed. The number of reference cells in the fourth cell image obtained is 400. Since the sum (i.e., 1000) of the number of reference cells in the first cell image, the number of reference cells in the second cell image, the number of reference cells in the third cell image and the number of reference cells in the fourth cell image is equal to the second threshold, the processor 15 acquires the number of reference cells in the blood sample to be tested, and calculates the number of target cells in the blood sample to be tested based on the sum of the numbers of reference cells in all cell images of the blood specimen, the sum of the numbers of target cells in all cell images of the blood specimen, and the number of reference cells in the blood sample to be tested.

The second threshold may be set in advance and stored in a memory (for example, a nonvolatile memory) of the cell image analysis apparatus 10. For example, the second threshold may be set as 1000. The first threshold may be the same as or different from the second threshold, which is not limited in the embodiments of the present disclosure.

Optionally, the processor may also simultaneously acquire at least two cell images of the blood specimen, automatically identify the at least two cell images of the blood specimen, and obtain the number (sum) of the reference cells and/or the number (sum) of the target cells in the at least two cell images, and then determine whether the number (sum) of the reference cells obtained in the cell images of the blood specimen is greater than or equal to the first threshold (or the second threshold). For subsequent steps, reference may be made to those described above.

In the embodiments of the present disclosure, a communication connection is established between the cell image analysis apparatus 10 and the blood analyzer 30. The cell image analysis apparatus 10 may automatically acquire the number of reference cells in the blood sample to be tested from the blood analyzer 30. The blood analyzer 30 may perform routine blood tests to estimate the number of reference cells in the blood sample to be tested. The cell image analysis apparatus 10 may estimate the number of target cells in the blood sample to be tested according to the number of reference cells measured by the blood analyzer 30.

Optionally, in the case where a communication connection is not established between the cell image analysis apparatus 10 and the blood analyzer 30, the cell image analysis apparatus 10 may receive the number of reference cells in the blood sample to be tested input by the user. The cell image analysis apparatus 10 may further include an inputting apparatus. The inputting apparatus may include a mouse, a keyboard, a display screen, and the like. For example, the user may input the number of reference cells in the blood sample to be tested to the cell image analysis apparatus 10 through the inputting apparatus. In addition, optionally, even if the cell image analysis apparatus 10 is in communication with the blood analyzer 30, the cell image analysis apparatus 10 may receive the number of reference cells in the blood sample to be tested input by the user, if necessary.

Figure 1B:
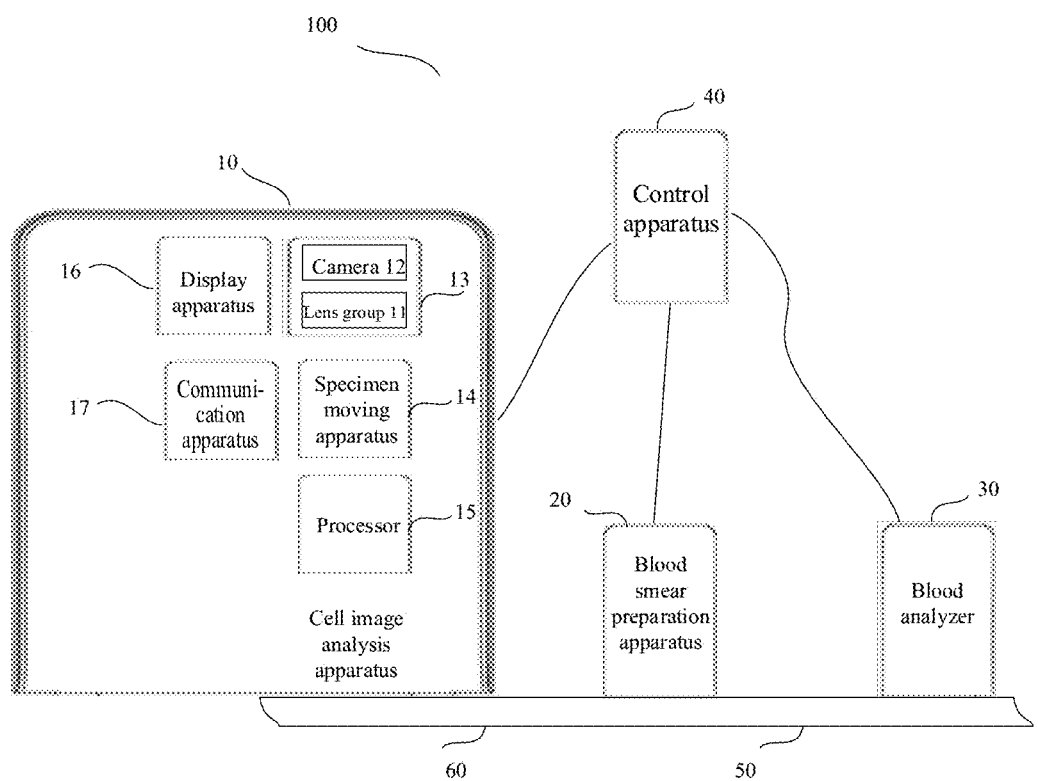
FIG. 1B illustrates a schematic structure diagram of another specimen analysis system disclosed in an embodiment of the present disclosure.
Figure 4:
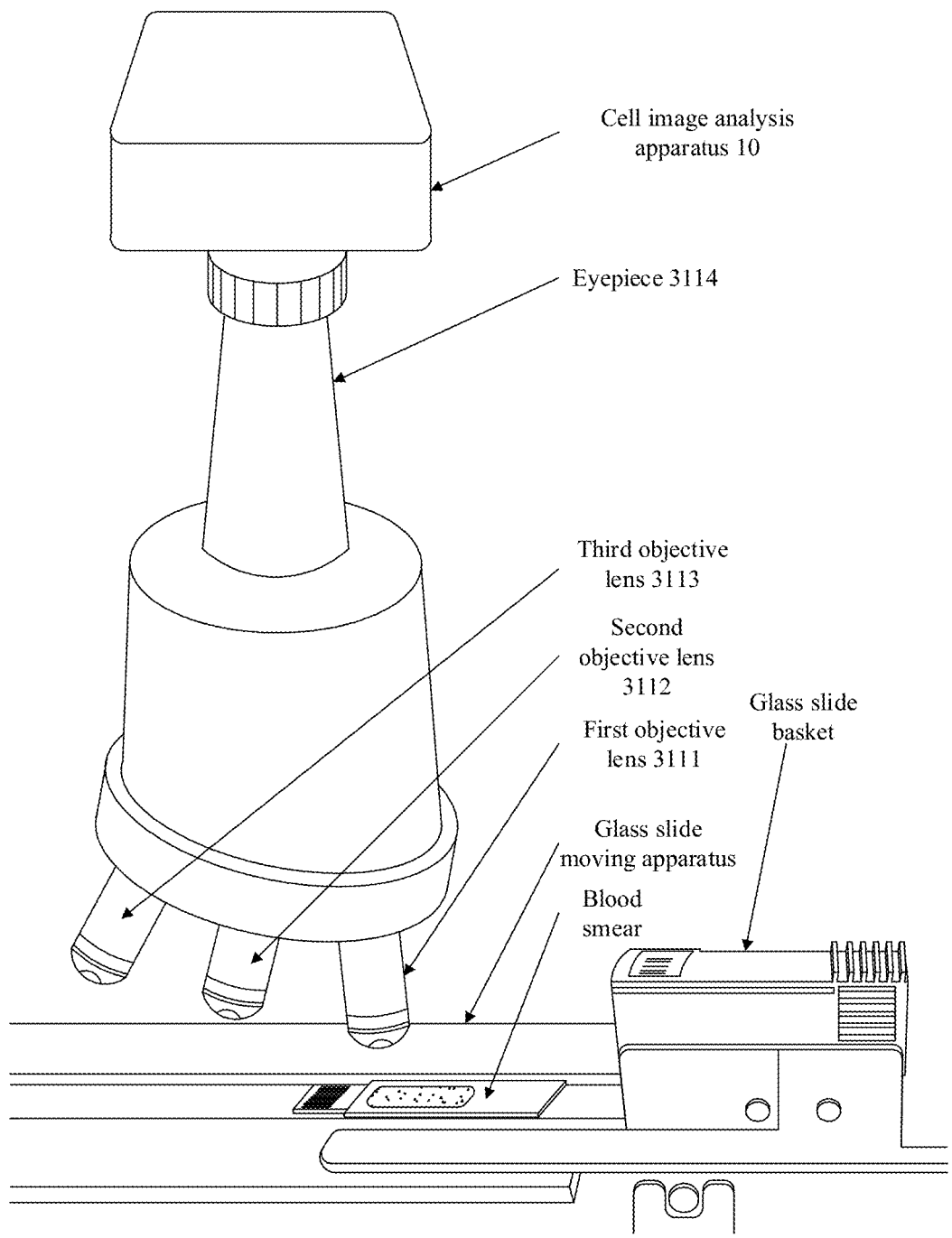
FIG. 4 illustrates a schematic structure diagram of the operation of a cell image analysis apparatus disclosed in an embodiment of the present disclosure.

Optionally, as illustrated in FIG. 1B, the specimen analysis system 100 further includes a control apparatus 40 that is connected with the blood analyzer 30, the blood smear preparation apparatus 20 and the cell image analysis apparatus 10, respectively. The cell image analysis apparatus 10 may communicate with the blood smear preparation apparatus 20 through the control apparatus 40, and may also communicate with the blood analyzer 30 through the control apparatus 40. The control apparatus is configured to control a transport device to transport the blood sample to be tested from the blood analyzer to the blood smear preparation apparatus, and is further configured to control the transport device to transport the blood smear prepared by the blood smear preparation apparatus to the cell image analysis apparatus Optionally, as illustrated in FIG. 4, the lens group 11 may include a first objective lens 3111, a second objective lens 3112 and an eyepiece 3114 (the eyepiece is optional). The first objective lens 3111 may be, for example, a 10× objective lens, and the second objective lens 3112 may be, for example, a 100× objective lens. The lens group 311 may further include a third objective lens 3113, and the third objective lens 3113 may be, for example, a 40× objective lens.

In the embodiments of the present disclosure, after the processor 15 acquires the cell image of the blood specimen, the processor 15 may identify the number of target cells and the number of reference cells in the cell image by using an image processing algorithm. The image processing algorithm may include one or more of an image segmentation algorithm and a deep neural network algorithm.

In the embodiments of the present disclosure, after the number of target cells and the number of reference cells in the cell image and the number of reference cells in the blood sample to be tested are acquired, the ratio of the number of target cells to the number of reference cells in the cell image can be obtained, and the number of target cells in the blood sample to be tested can be obtained by multiplying the ratio of the number of target cells to the number of reference cells in the cell image by the number of reference cells in the blood sample to be tested.

In the embodiments of the present disclosure, the number of target cells in the blood sample to be tested can be accurately calculated. Compared with the manual counting method, the inspector does not need to count the target cells under the microscope for a long time, the counting efficiency of the target cells is improved, while manual errors are avoided.

Figure 5:
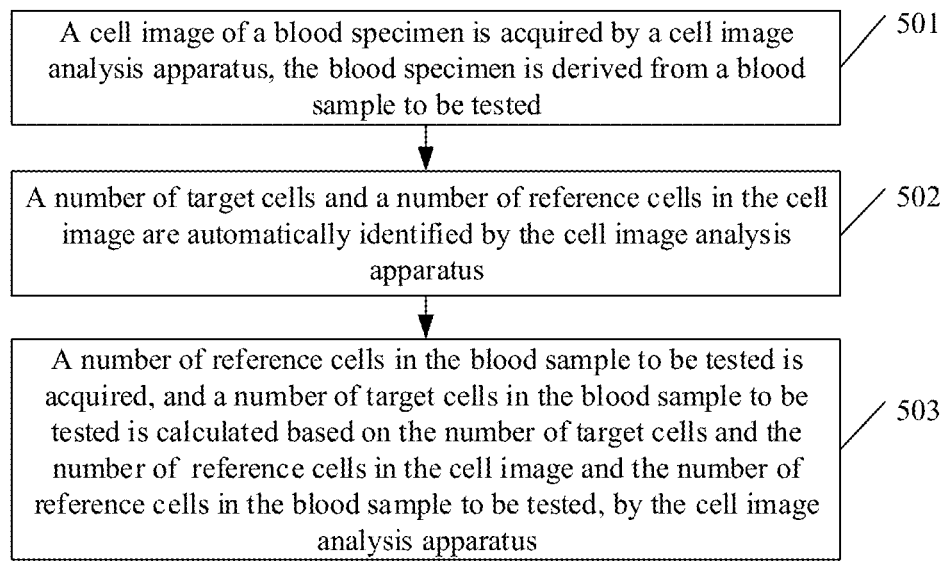
FIG. 5 illustrates a schematic flowchart of a target cell statistical method disclosed in an embodiment of the present disclosure.

With reference to FIG. 5, FIG. 5 illustrates a schematic flowchart of a target cell statistical method disclosed in an embodiment of the present disclosure. The method illustrated in FIG. 5 may be applied to the cell image analysis apparatus in the specimen analysis system illustrated in FIG. 1. The method includes the following steps.

In 501, a cell image of a blood specimen is acquired by a cell image analysis apparatus. The blood specimen is derived from a blood sample to be tested.

In the embodiments of the present disclosure, in the case where the cell image analysis apparatus does not have a photographing function, or the photographing apparatus of the cell image analysis apparatus is damaged and cannot be operated, the cell image analysis apparatus may receive the cell image of the blood specimen input from other devices through an I/O interface (for example, a USB interface). The cell image of the blood specimen may be pre-stored by other devices, or may be photographed by other devices. The cell image analysis apparatus may also receive the cell image of the blood specimen sent by the server through the communication interface. The cell image analysis apparatus may also receive the cell image of the blood specimen input by the user.

In the case where the cell image analysis apparatus has a photographing function, the cell image analysis apparatus may also receive the cell image of the blood specimen photographed by the photographing apparatus.

The blood sample to be tested is a blood sample which needs to be tested, and the blood specimen is a small amount of the blood sample to be tested and is taken from the blood sample to be tested. For example, the blood sample to be tested is 5 ml of blood. The blood specimen may be then 0.05 ml of blood. The blood specimen may be loaded on the glass slide and presented as a blood smear. For details of the preparation of the blood smear, reference may be made to the system embodiment illustrated in FIG. 1, which will not be repeated herein.

In 502, a number of target cells and a number of reference cells in the cell image are automatically identified by the cell image analysis apparatus.

In the embodiments of the present disclosure, the target cells and reference cells are different blood cells. For example, when the target cells are blood platelets, the reference cells may include one of red blood cells, white blood cells, or a combination of red blood cells and white blood cells. When the target cells are red blood cells, the reference cells may include one of white blood cells, blood platelets, or a combination of white blood cells and blood platelets. When the target cells are white blood cells, the reference cells may include one of red blood cells, blood platelets, or a combination of red blood cells and blood platelets.

Optionally, step 502 may specifically include the following step.

The cell image analysis apparatus identifies blood platelets and the reference cells in the cell image, and counts a number of blood platelets and the number of reference cells, by using an image processing method.

The image processing method may include an image segmentation method or a deep learning method.

In 503, a number of reference cells in the blood sample to be tested is acquired, and a number of target cells in the blood sample to be tested is calculated based on the number of target cells and the number of reference cells in the cell image and the number of reference cells in the blood sample to be tested, by the cell image analysis apparatus.

In the embodiments of the present disclosure, in the case where a communication connection is established between the cell image analysis apparatus and the blood analyzer, the cell image analysis apparatus may automatically acquire the number of reference cells in the blood sample to be tested from the blood analyzer. The cell image analysis apparatus may also receive the number of reference cells in the blood sample to be tested input by the user, such as in the case where a communication connection is not established between the cell image analysis apparatus and the blood analyzer. In addition, optionally, even if there is a communication connection between the two, the cell image analysis apparatus may receive the number of reference cells in the blood sample to be tested which is input by the user.

The blood analyzer may detect the blood sample to be tested to obtain the detection result of reference cells in the blood sample to be tested. The detection result of reference cells may include the total number of reference cells, the number of reference cells per milliliter of blood, and the like. For example, the blood analyzer may print out the cell detection result or display it through the display apparatus of the blood analyzer. The user may input the number of reference cells (for example, the concentration) shown in the printed cell detection result or the cell detection result displayed by the display apparatus into the cell image analysis apparatus. The user may input the total number of reference cells to the cell image analysis apparatus through an I/O interface (for example, a USB interface). Specifically, the cell image analysis apparatus may be connected with a keyboard, a mouse through an I/O interface (for example, a USB interface), and the user inputs the total number of reference cells to the cell image analysis apparatus through the keyboard and the mouse.

When the cell image analysis apparatus acquires the number of target cells and the number of reference cells in the cell image, and the number of reference cells in the blood sample to be tested, the ratio of the number of target cells to the number of reference cells in the cell image may be obtained, and the number of target cells in the blood sample to be tested may be obtained by multiplying the ratio of the number of target cells to the number of reference cells in the cell image by the number of reference cells in the blood sample to be tested.

Optionally, after step 502 is performed and before step 503 is performed, the following steps may also be performed.

The cell image analysis apparatus determines whether the number of target cells in the cell image exceeds a first preset number threshold.

If it exceeds the first preset number threshold, step 503 is performed.

If it does not exceed the first preset number threshold, step 501 to step 502 are further performed until the number of target cells cumulatively counted by the cell image analysis apparatus for a plurality of times exceeds the first preset number threshold, and then step 503 is performed.

The first preset number threshold may be preset and stored in the nonvolatile memory of the cell image analysis apparatus. For example, the first preset number threshold may be set as 1000. In the embodiments of the present disclosure, the number of reference cells in a plurality of cell images of a blood specimen may be cumulatively counted, thereby improving statistical accuracy and avoiding large statistical errors.

Step 503 includes: the cell image analysis apparatus acquires the number of reference cells in the blood sample to be tested, and calculates the number of target cells in the blood sample to be tested based on the number of target cells cumulatively counted for a plurality of times and the number of reference cells cumulatively counted for a plurality of times, and the number of reference cells in the blood sample to be tested.

The number of target cells in the blood sample to be tested may be calculated according to the following formula:

$$N_{PLT} = \frac{M_{PLT}}{M_{RFBC}} \cdot N_{RFBC}$$

In the formula, $N_{PLT}$ is the number of target cells in the blood sample to be tested, $N_{RFBC}$ is the number of reference cells in the blood sample to be tested, $M_{PLT}$ is the number of target cells cumulatively counted for a plurality of times, and $M_{RFBC}$ is the number of reference cells cumulatively counted for a plurality of times.

Optionally, after step 502 is performed and before step 503 is performed, the following steps may also be performed.

The cell image analysis apparatus determines whether the number of target cells in the cell image exceeds a first preset number threshold.

If it exceeds the first preset number threshold, step 503 is performed.

If it does not exceed the first preset number threshold, step 501 to step 502 are further performed until the number of target cells counted by the cell image analysis apparatus exceeds the first preset number threshold, and then step 503 is performed.

Optionally, the cell image analysis apparatus displays the number of target cells in the blood sample to be tested.

Optionally, the cell image analysis apparatus transmits the number of target cells in the blood sample to be tested to other devices for display.

After the cell image analysis apparatus calculates the number of target cells in the blood sample to be tested, the number of target cells in the blood sample to be tested may be displayed on the display apparatus of the cell image analysis apparatus, or the number of target cells in the blood sample to be tested which is obtained by calculation may be displayed on other devices that communicate with the cell image analysis apparatus and have a display function, which is not limited in the embodiments of the present disclosure.

Optionally, the other devices include at least one of the blood analyzer, the blood smear preparation apparatus, or the terminal device shown in FIG. 1A or FIG. 1B.

In the embodiments of the present disclosure, the number of target cells in the blood sample to be tested can be accurately calculated. Compared with the manual counting method, the inspector does not need to count the target cells under the microscope for a long time, the counting efficiency of the target cells is improved, while manual errors are avoided.

Figure 6:
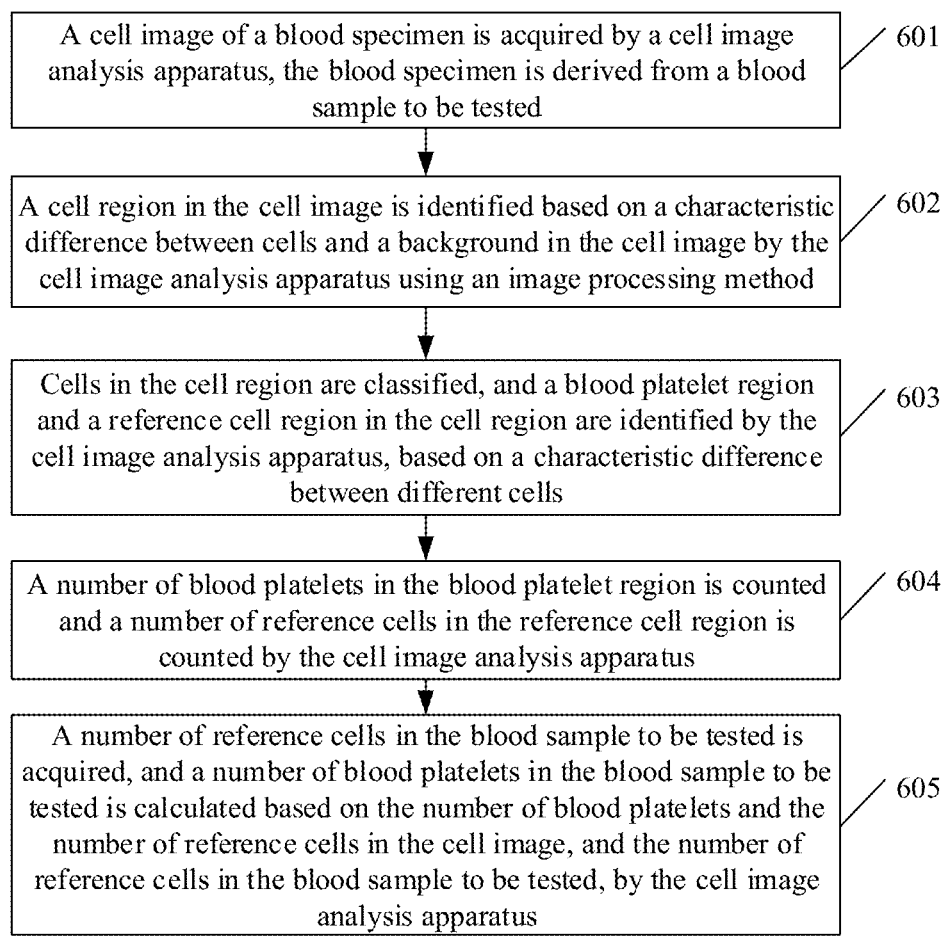
FIG. 6 illustrates a schematic flowchart of another target cell statistical method disclosed in an embodiment of the present disclosure.

With reference to FIG. 6, FIG. 6 illustrates a schematic flowchart of another target cell statistical method disclosed in an embodiment of the present disclosure. FIG. 6 is obtained by further optimization on the basis of FIG. 5. The method illustrated in FIG. 6 may be applied to the cell image analysis apparatus in the specimen analysis system illustrated in FIG. 1. The method includes the following steps.

In 601, a cell image of a blood specimen is acquired by a cell image analysis apparatus. The blood specimen is derived from a blood sample to be tested.

As for the specific implementation of step 601, step 501 illustrated in FIG. 5 may be referred to, which will not be repeated herein.

In 602, a cell region in the cell image is identified based on a characteristic difference between cells and a background in the cell image by the cell image analysis apparatus using an image processing method.

The image processing method may include an image segmentation method.

In the embodiments of the present disclosure, the characteristic difference between the cells and the background in the cell image may include the grayscale difference, the difference in the component of specific color space. The specific color space may comprise hue saturation intensity (HSI) color space, hue saturation value (HSV) color space, and red green blue (RGB) color space etc. For example, the cell region and the background region in the cell image may be determined according to the grayscale histogram of the cell image.

Optionally, step 602 may include the following step.

The cell region in the cell image is identified by performing grayscale processing on the cell image based on the grayscale difference between the cells and the background in the cell image by cell image analysis apparatus.

In the embodiments of the present disclosure, the cell image analysis apparatus may acquire a grayscale histogram of the cell image, and identify the cell region in the cell image according to the grayscale difference between the cell region and the background region in the grayscale histogram.

Optionally, step 602 may include the following step.

The cell region in the cell image is identified based on the color difference and brightness difference between the cells and the background in the cell image by the cell image analysis apparatus using the image segmentation method with edge detection.

In the embodiments of the present disclosure, based on the image segmentation method with edge detection, according to significant differences in color and brightness between the cells and the background, that is, a relatively apparent edge is present, the cell image analysis apparatus can detect the edge of the cell by a gradient, so as to separate the cells from the background.

Optionally, step 602 may include the following step.

The cell region in the cell image is identified based on the color difference and brightness difference between the cells and the background in the cell image by the cell image analysis apparatus using the image segmentation method on basis of region splitting and merging.

In the embodiments of the present disclosure, the image segmentation method on basis of region splitting and merging is as follows. On the basis that there are significant differences in color and brightness between the cells and the background, whereas color and brightness are highly consistent inside the background or inside the cells, the picture can be divided into a plurality of small regions according to the similarity, and then the adjacent similar regions are merged, so as to separate the cells from the background.

Optionally, step 602 may include the following step.

The cell region in the cell image is identified based on the brightness difference between the cells and the background in the cell image by the cell image analysis apparatus using the image segmentation method on basis of watershed algorithm.

In the embodiments of the present disclosure, the image background of the cell image is brighter, which can be regarded as a terrain surface. The cell region of the cell image is darker, which can be regarded as a valley. The boundary line between the valley and the terrain surface is obtained by adopting the watershed algorithm, that is, the edge line between the cells and the background, so as to separate the cells from the background.

Figure 7A:
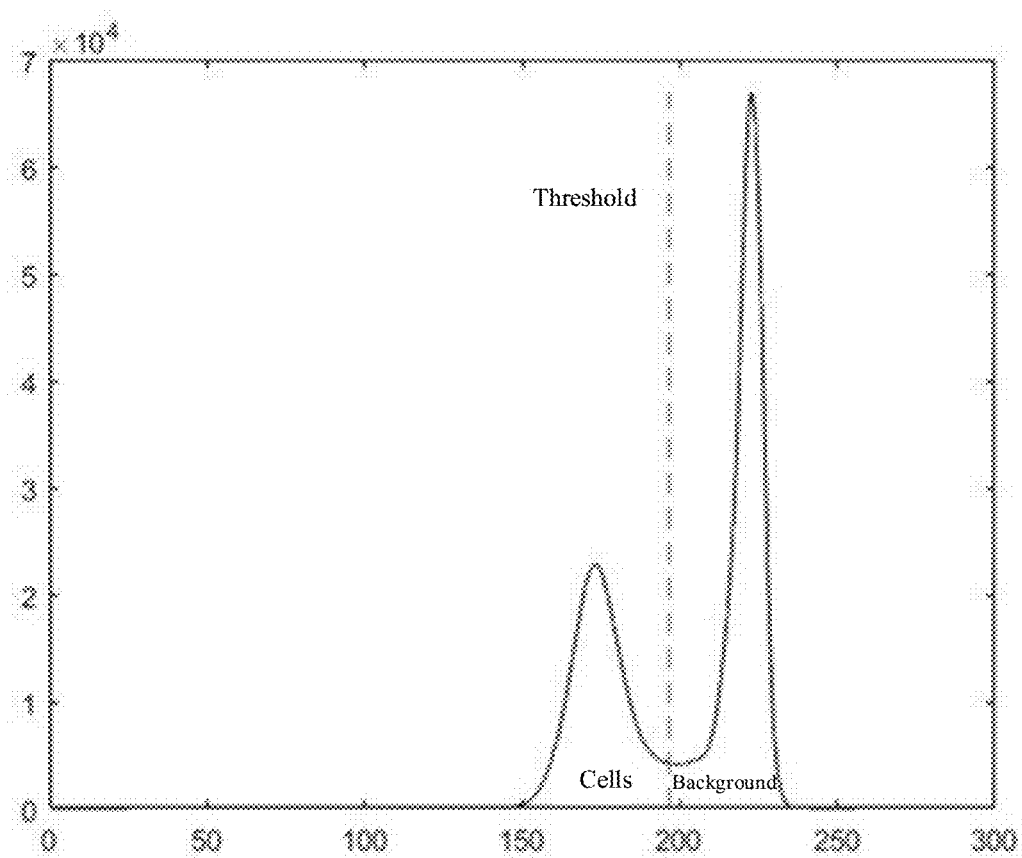
FIG. 7A illustrates a grayscale histogram of a cell image disclosed in an embodiment of the present disclosure.
Figure 8A:
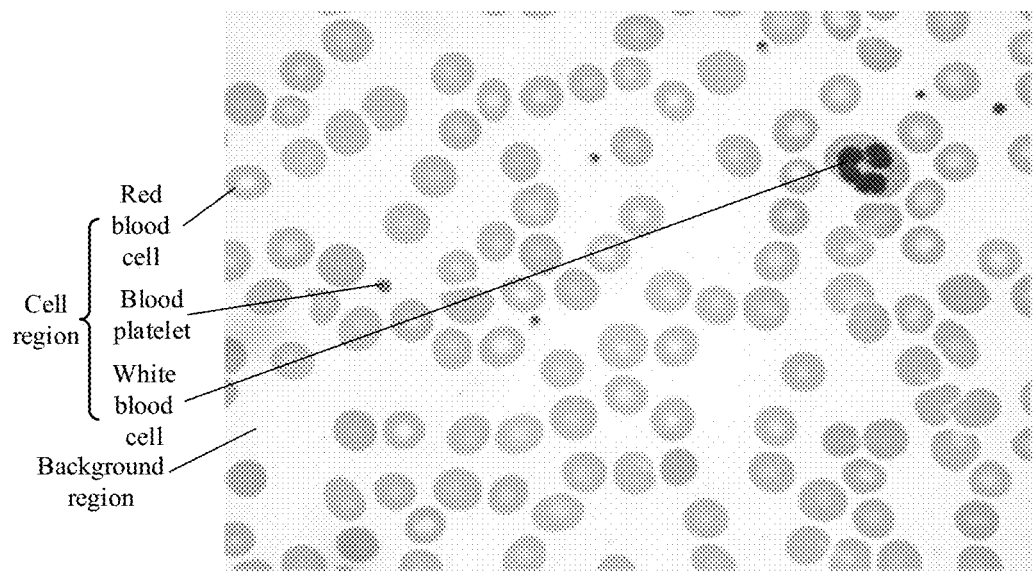
FIG. 8A illustrates a schematic diagram of a cell image disclosed in the embodiment of the present disclosure.

Specifically referring to FIG. 7A, FIG. 7A illustrates a grayscale histogram of a cell image disclosed in an embodiment of the present disclosure. As illustrated in FIG. 7A, the abscissa of the grayscale histogram is a grayscale value of a pixel of the cell image, and the ordinate is the number of pixels corresponding to the grayscale value. As illustrated in FIG. 7A, the grayscale value of the cell region is between 100 and 200, and the grayscale value of the background is between 200 and 255. The cell image analysis apparatus can determine the region where the grayscale value of the pixel of the cell image is between 100 and 200 as the cell region, and determine the region where the grayscale value of the pixel of the cell image is between 200 and 255 as the background region. It should be noted that regions of red blood cells that do not have cell nuclei is prone to be determined as the background region in some cases (for example, middle regions of red blood cells in cell images photographed at the body-tail junction, middle region of red blood cells in a hypochromic blood specimen photographed), since mature red blood cells do not have cell nuclei. The background region surrounded by the cell region (the extremely light-colored region in the middle of the red blood cell as shown in FIG. 8A) can be determined as the cell region.

Optionally, step 602 may include the following step.

The cell image analysis apparatus identifies the cell region in the cell image by performing specific color space conversion on the cell image based on the difference in component of the specific color space between the cells and the background in the cell image.

In the embodiments of the present disclosure, the specific color space includes one of RGB color space, HSV color space, HSI color space, Lab color space, luminance chrominance (YUV) color space, or luminance chrominance blue chrominance red (YCbCr) color space. The component of the specific color space includes any component in RGB color space or any component in HSV color space or any component in HSI color space or any component in Lab color space or any component in YUV color space or any component in YCbCr color space.

For example, the cell image analysis apparatus distinguishes the cell region and the background region in the cell image based on the R component of the RGB color space of the cells and the background in the cell image.

In 603, cells in the cell region are classified, and a blood platelet region and a reference cell region in the cell region are identified by the cell image analysis apparatus, based on a characteristic difference between different cells.

In the embodiments of the present disclosure, the characteristic difference between the blood platelet and the reference cell in the cell region may include the difference in the component of specific color space (for example, HSI color space, HSV color space) and the difference in cell size. For example, when the reference cell is a red blood cell, the cell image analysis apparatus may identify the red blood cell and the blood platelet according to the difference in the S component in the HSI color space of the cell image. For example, for 8-bit HSI, the S component of the blood platelets and nucleated cells (such as the nuclei of white blood cells) is generally between 150 and 255, and the S component of red blood cells is generally between 0 and 150. The red blood cell region and the blood platelet white blood cell region (that is, the first region) in the cell image may be distinguished according to the size of the S component in the cell image. The cell image analysis apparatus distinguishes a blood platelet region and a white blood cell region (that is, a white blood cell nucleus region) in the blood platelet white blood cell region according to the size of the connected regions in the blood platelet white blood cell region.

The connected region includes an eight-connected region or a four-connected region.

The eight-connected region refers to a region where any pixel in the region can be reached starting from each pixel in the region, through the combination of movement in eight directions, that is, up, down, left, right, upper left, upper right, lower left, and lower right, without going beyond the region.

The four-connected region refers to a region where any pixel in the region can be reached starting from each pixel in the region, through the combination of movement in four directions, that is, up, down, left, and right, without going beyond the region.

In general, the diameter of white blood cell nucleus is larger than that of blood platelet. The cell image analysis apparatus may distinguish white blood cell nuclei and blood platelets according to the cell size of white blood cell nuclei and blood platelets.

Optionally, step 603 may include the following step.

The cell image analysis apparatus classifies the cells in the cell region and identifies the blood platelet region and the reference cell region in the cell region based on the characteristic difference between different cells by using one of the support vector machine method, the artificial neural network method or the Bayesian method.

The characteristic difference includes the difference in characteristics such as average grayscale, variance, and area.

Optionally, step 603 may include the following steps.

(11) The cell image analysis apparatus identifies a red blood cell region and a first region in the cell region based on the difference in component of the specific color space between the red blood cells and a first type of cells in the cell region. The first type of cells includes white blood cells and blood platelets, and the first region includes a white blood cell region and the blood platelet region in the cell region.

In the embodiments of the present disclosure, the first type of cells includes blood platelets and nucleated cells (for example, white blood cells). The specific color space includes one of RGB color space, HSV color space, HSI color space, Lab color space, YUV color space or YCbCr color space. The component of the specific color space includes any component in RGB color space or any component in HSV color space or any component in HSI color space or any component in Lab color space or any component in YUV color space or any component in YCbCr color space.

For example, the S component of the HSV color space or the HSI color space is taken as an example. The S component of red blood cells is generally between 0 and 150, and the S component of blood platelets and white blood cells is generally between 150 and 255. The red blood cell region and the first region (that is, the regions of blood platelets and white blood cell nuclei) in the cell image may be distinguished according to the size of the S component in the cell image.

Figure 7B:
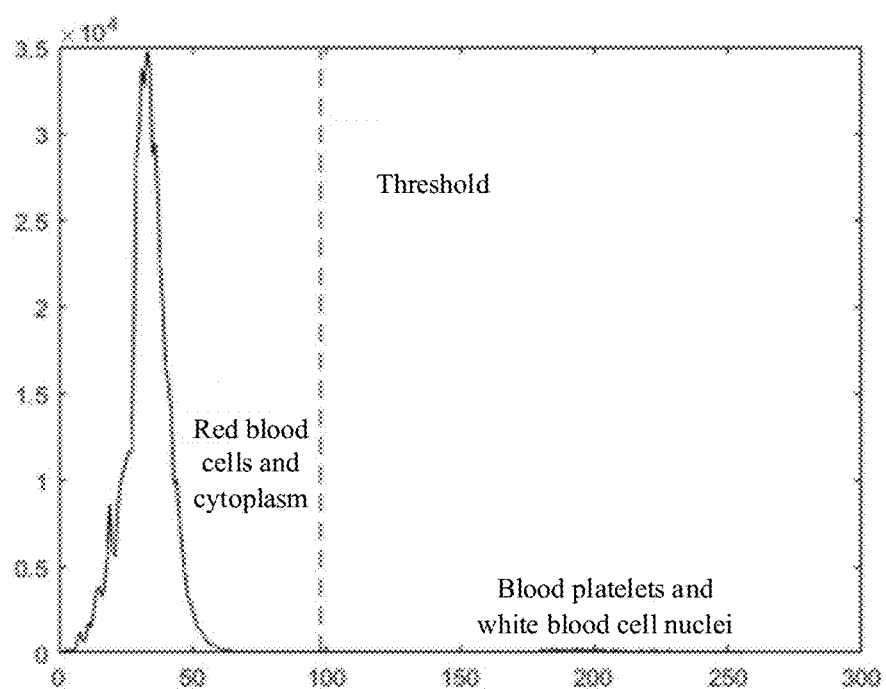
FIG. 7B illustrates an S-component histogram of a cell image disclosed in an embodiment of the present disclosure.

Specifically, with reference to FIG. 7B, FIG. 7B illustrates an S component histogram of a cell image disclosed in an embodiment of the present disclosure. As illustrated in FIG. 7B, the abscissa of the S component histogram is an S component value of the cell image, and the ordinate is the number of pixels corresponding to the S component value of the cell image. As illustrated in FIG. 7B, the S component value of red blood cells is between 0 and 150 (the S component value of the cytoplasm of white blood cells is also between 0 and 150), and the S component value of blood platelets and nucleated cells (that is, the nuclei of white blood cells) is between 150 and 255. The cell image analysis apparatus may determine a region where the S component value of the cell image is between 150 and 255 as the first region, and determine the region where the S component value of the cell image is between 0 and 150 as the red blood cell region.

(12) The cell image analysis apparatus identifies the blood platelet region in the first region, or identifies the white blood cell region and the blood platelet region in the first region, based on the difference in area between the white blood cells and blood platelets in the first region.

In the embodiments of the present disclosure, the difference in area between the white blood cells and the blood platelets in the first region is based on the difference in area between the white blood cell nuclei and the blood platelets in the first region. Generally speaking, the diameter of a white blood cell nucleus is larger than that of a blood platelet, and the area of a white blood cell nucleus is larger than that of a blood platelet. The cell image analysis apparatus identifies the blood platelet region in the first region, or identifies the white blood cell region (that is, the white blood cell nucleus region) and the blood platelet region in the first region, based on the difference in area of the white blood cell nuclei and blood platelets in the first region.

When the reference cells include red blood cells, the reference cell region includes the red blood cell region. When the reference cells include white blood cells, the reference cell region includes the white blood cell region. When the reference cells include a combination of red blood cells and white blood cells, the reference cell region includes the red blood cell region and the white blood cell region.

In 604, a number of blood platelets in the blood platelet region is counted and a number of reference cells in the reference cell region is counted by the cell image analysis apparatus.

In the embodiments of the present disclosure, red blood cells are taken as the reference cells as an example. After filling the multi-connected regions in the red blood cell region, the cell image analysis apparatus may count the number of single-connected regions in the red blood cell region, so as to obtain the number of red blood cells in the cell image. The cell image analysis apparatus counts the number of blood platelet connected regions in the blood platelet region, so as to obtain the number of blood platelets in the cell image of the specified region.

Optionally, step 604 may include the following steps.

(21) When the reference cells include red blood cells, the cell image analysis apparatus counts the number of blood platelets in the blood platelet region, and counts the number of red blood cells in the red blood cell region.

(22) When the reference cells include white blood cells, the cell image analysis apparatus counts the number of blood platelets in the blood platelet region, and counts the number of corresponding white blood cells in the white blood cell region.

(23) When the reference cells include a combination of red blood cells and white blood cells, the cell image analysis apparatus counts the number of blood platelets in the blood platelet region, counts the number of red blood cells in the red blood cell region, and counts the number of corresponding white blood cells in the white blood cell region.

Optionally, in step (21) to step (23), that the cell image analysis apparatus counts the number of blood platelets in the blood platelet region, may specifically include the following step.

The cell image analysis apparatus counts the number of connected regions in the blood platelet region, and takes the number of connected regions in the blood platelet region as the number of blood platelets in the blood platelet region.

Optionally, the connected region includes an eight-connected region or a four-connected region.

Optionally, that the cell image analysis apparatus counts the number of reference cells in the reference cell region, may specifically include the following steps.

(31) When the reference cell includes red blood cells, the cell image analysis apparatus fills holes in a multi-connected region in the red blood cell region to form a single-connected region, and determines the number of reference cells in the reference cell region according to the parameter of the single-connected region in the red blood cell region.

(32) When the reference cell includes white blood cells, the cell image analysis apparatus counts the number of connected regions in the white blood cell region, and takes the number of connected regions in the white blood cell region as the number of reference cells in the reference cell region. Optionally, the connected region includes an eight-connected region or a four-connected region.

(33) When the reference cell includes a combination of red blood cells and white blood cells, the cell image analysis apparatus counts the number of connected regions in the white blood cell region, and determines the number of white blood cells in the reference cell region according to the number of connected regions in the white blood cell region. The cell image analysis apparatus fills holes in the multi-connected region in the red blood cell region to form a single-connected region, and determines the number of red blood cells in the reference cell region according to the parameter of the single-connected region in the red blood cell region. The cell image analysis apparatus takes the sum of the number of white blood cells in the reference cell region and the number of red blood cells in the reference cell region as the number of reference cells in the reference cell region. Alternatively, the cell image analysis apparatus takes the number of white blood cells in the reference cell region and the number of red blood cells in the reference cell region respectively as the number of reference cells in the reference cell region.

Optionally, the parameter of the single-connected region includes the number of single-connected regions. That the cell image analysis apparatus determines the number of reference cells in the reference cell region according to the parameter of the single-connected region in the red blood cell region, includes the following.

The cell image analysis apparatus counts the number of single-connected regions in the red blood cell region, and takes the number of single-connected regions in the red blood cell region as the number of reference cells in the reference cell region.

That the cell image analysis apparatus determines the number of red blood cells in the reference cell region according to the parameter of the single-connected region in the red blood cell region, includes the following.

The cell image analysis apparatus counts the number of single-connected regions in the red blood cell region, and takes the number of single-connected regions in the red blood cell region as the number of red blood cells in the reference cell region.

The embodiment of the present disclosure may be applied to the situation where there is no influence of other impurities (for example, the cytoplasm of white blood cells, the transparent region of blood platelets) in the red blood cell region, and the number of red blood cells in the reference cell region can be accurately counted by only counting the number of single-connected regions in the red blood cell region.

Optionally, the parameter of the single-connected region includes the number of single-connected regions and the area of the single-connected regions. That the cell image analysis apparatus determines the number of reference cells in the reference cell region according to the parameter of the single-connected region in the red blood cell region, includes the following.

The cell image analysis apparatus counts the number of single-connected regions with an area in a preset area threshold interval in the red blood cell region, and takes the number of single-connected regions with an area in a preset area threshold interval in the red blood cell region as the number of reference cells in the reference cell region.

That the cell image analysis apparatus determines the number of red blood cells in the reference cell region according to the parameter of the single-connected region in the red blood cell region, includes the following.

The cell image analysis apparatus counts the number of single-connected regions with an area in a preset area threshold interval in the red blood cell region, and takes the number of single-connected regions with an area in a preset area threshold interval in the red blood cell region as the number of red blood cells in the reference cell region.

In the embodiment of the present disclosure, in the case where there is impurity influence in the red blood cell region, for example, when the cytoplasm of white blood cells exists in the red blood cell region, single-connected regions will also be formed when the connected region formed by the cytoplasm of white blood cells is filled. If the area of a single-connected region is not considered, these single-connected regions may affect the counting results of red blood cells.

Generally speaking, the area of the single-connected region formed by the cytoplasm of white blood cells is larger than that of the single-connected region formed by the red blood cells, and the area of the single-connected region formed by the transparent region of the blood platelets is smaller than that of the single-connected region formed by the red blood cells. A preset area threshold interval can be set, so that the area of the single-connected region formed by red blood cells falls within the preset area threshold interval, so that the area of the single-connected region formed by the cytoplasm of white blood cells does not fall within the preset area threshold interval, so that the area of the single-connected region formed by the transparent region of the blood platelets does not fall within the preset area threshold interval.

In the case where the reference cells include a combination of red blood cells and white blood cells, the cell image analysis apparatus counts the number of red blood cells in the red blood cell region, counts the number of white blood cells in the white blood cell region, takes the number of red blood cells in the red blood cell region as the number of first reference cells and takes the number of white blood cells in the white blood cell region as the number of second reference cells.

A single-connected region is defined as follows. In a region designated as D, if the interior of any simple closed curve in D all belongs to D, then D is referred to as a single-connected region. The single-connected region may also be described as follows: the region enclosed by any closed curve in D contains only the points of D. More informally, the single-connected region is a region without "holes".

A multi-connected region is defined as follows. In a region designated as D, if there is a simple closed curve in D, and the interior of the simple closed curve does not belong to D, then D is referred to as a multi-connected region. More informally, a multi-connected region is a region with "holes".

The cell image analysis apparatus acquires the number of reference cells in the blood sample to be tested, and calculates the number of blood platelets in the blood sample to be tested, based on the number of blood platelets, the number of first reference cells, the number of second reference cells in the cell image, and the number of first reference cells, the number of second reference cells in the blood sample to be tested.

In 605, a number of reference cells in the blood sample to be tested is acquired, and a number of blood platelets in the blood sample to be tested is calculated based on the number of blood platelets and the number of reference cells in the cell image, and the number of reference cells in the blood sample to be tested, by the cell image analysis apparatus.

As for the specific implementation of step 605, step 503 illustrated in FIG. 5 may be referred to, which will not be repeated herein.

Optionally, step 605 may include the following steps.

The cell image analysis apparatus calculates the number of target cells in the blood sample to be tested according to the following formula:

$$N_{PLT} = \frac{M_{PLT}}{M_{RFBC}} \cdot N_{RFBC}$$

In the formula, $N_{PLT}$ is the number of blood platelets in the blood sample to be tested, $N_{RFBC}$ is the number of reference cells in the blood sample to be tested, $M_{PLT}$ is the number of blood platelets in the cell image, and $M_{RFBC}$ is the number of reference cells in the cell image. Reference cells may include red blood cells or white blood cells.

Optionally, step 605 may include the following step.

The cell image analysis apparatus calculates the number of target cells in the blood sample to be tested according to the following formula:

$$N_{PLT} = a \cdot \frac{M_{PLT}}{M_{RBC}} \cdot N_{RBC} + b \cdot \frac{M_{PLT}}{M_{WBC}} \cdot N_{WBC}$$

In the formula, $N_{PLT}$ is the number of blood platelets in the blood sample to be tested, $N_{RBC}$ is the number of red blood cells (first reference cells) in the blood sample to be tested, $N_{WBC}$ is the number of white blood cells (second reference cells) in the blood sample to be tested, and $M_{PLT}$ is the number of blood platelets in the cell image, $M_{RBC}$ is the number of red blood cells in the cell image (the first reference cells), and $M_{WBC}$ is the number of white blood cells in the cell image (the second reference cells). Reference cells include a combination of red blood cells and white blood cells. Among them, 0<a<1, 0<b<1, a+b=1. a and b are the weighting coefficients, respectively.

Optionally, 0<a<1, 0<b<1, a>b, a+b=1. Since the number of red blood cells is much more than the number of white blood cells in the blood, the error of counting red blood cell is relatively small. It can be considered that the weighting coefficient of red blood cells as reference cells is increased, and the weighting coefficient of white blood cells as reference cells is decreased, so as to further improve the calculation accuracy of the number of blood platelets.

Optionally, step 605 may include the following step.

The cell image analysis apparatus calculates the number of target cells in the blood sample to be tested according to the following formula:

$$N_{PLT} = \frac{M_{PLT}}{M_{RBC} + M_{WBC}} \times (N_{RBC} + N_{WBC})$$

In the formula, $N_{PLT}$ is the number of blood platelets in the blood sample to be tested, $N_{RBC}$ is the number of red blood cells (first reference cells) in the blood sample to be tested, $N_{WBC}$ is the number of white blood cells (second reference cells) in the blood sample to be tested, and $M_{PLT}$ is the number of blood platelets in the cell image, $M_{RBC}$ is the number of red blood cells (first reference cells) in the cell image, and $M_{WBC}$ is the number of white blood cells (second reference cells) in the cell image.

Optionally, when the target cells are white blood cells or red blood cells, the above calculation method may also be used, except that the target cells and reference cells in the formula are replaced with each other accordingly.

In order to better understand the target cell statistical method in the embodiments of the present disclosure, an example is provided in the following. In the example, blood platelets are the target cells, and red blood cells are the reference cells. The example will be described with reference to FIG. 8A to FIG. 8F.

In step 1, the cell image analysis apparatus acquires the cell image of the blood specimen.

In step 2, the cell image analysis apparatus identifies the cell region and the background region in the cell image.

In step 3, the cell image analysis apparatus identifies the red blood cell region and the blood platelet region in the cell region in the cell image.

In step 4, the cell image analysis apparatus counts the number of red blood cells in the red blood cell region and counts the number of blood platelets in the blood platelet region.

In step 5, the cell image analysis apparatus acquires the number of red blood cells in the blood sample to be tested, and calculates the number of blood platelets in the blood sample to be tested based on the number of blood platelets and the number of red blood cells in the cell image, and the number of red blood cells in the blood sample to be tested.

Figure 8B:
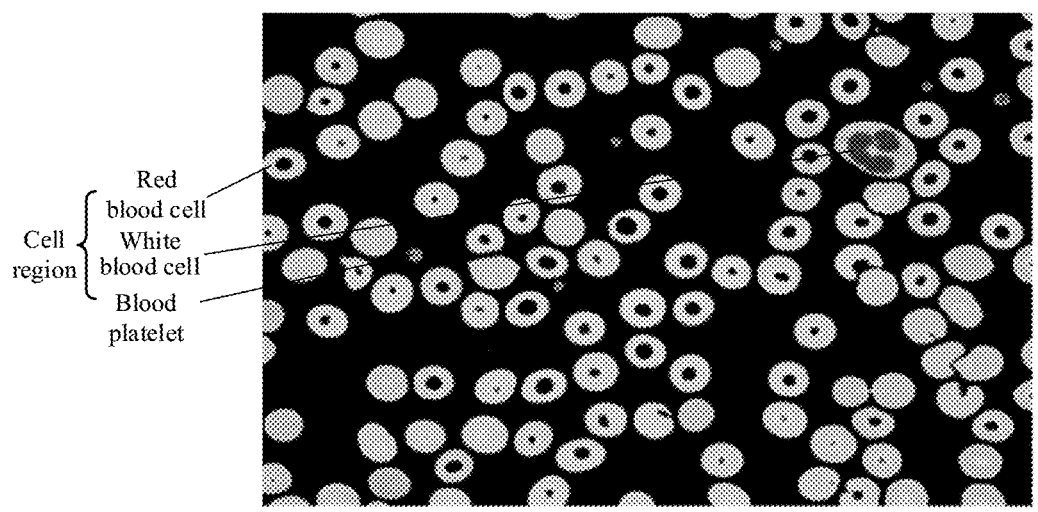
FIG. 8B illustrates a cell image processed by grayscale threshold segmentation disclosed in an embodiment of the present disclosure.
Figure 8C:
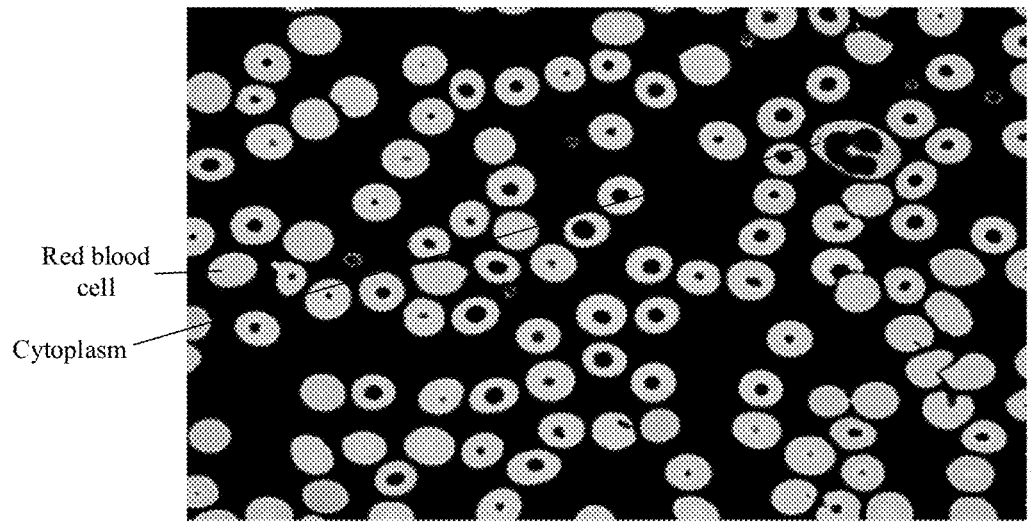
FIG. 8C illustrates an image of a red blood cell region including red blood cells and cytoplasm disclosed in an embodiment of the present disclosure.
Figure 8D:
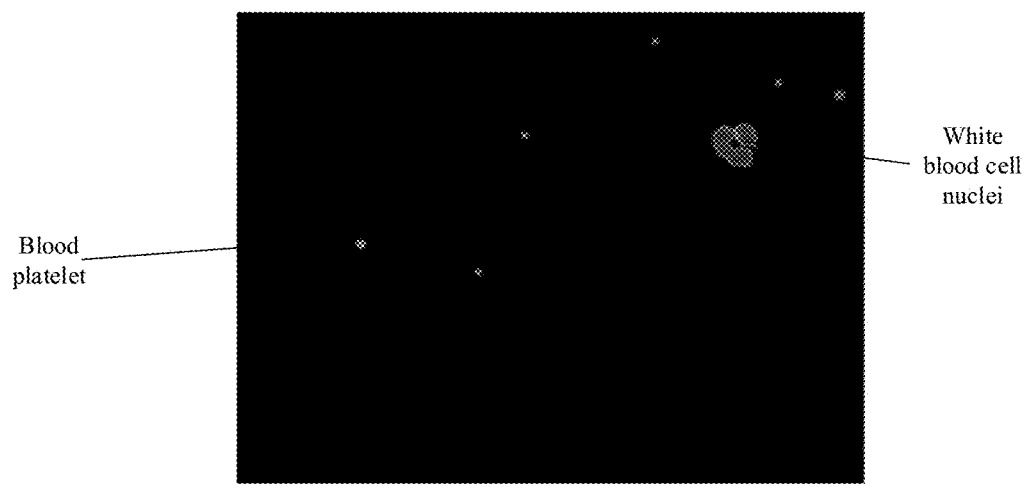
FIG. 8D illustrates an image of a first region including blood platelets and white blood cell nuclei disclosed in an embodiment of the present disclosure.
Figure 8E:
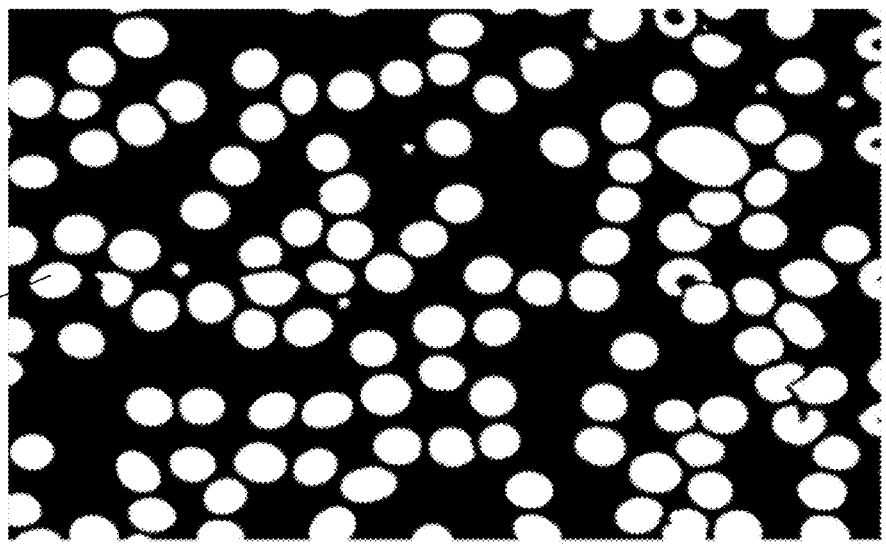
FIG. 8E illustrates an image of a filled red blood cell region including red blood cells and cytoplasm disclosed in an embodiment of the present disclosure.
Figure 8F:
FIG. 8F illustrates an image of a blood platelet region including blood platelets disclosed in an embodiment of the present disclosure.

With reference to FIG. 8A, FIG. 8A illustrates a schematic diagram of a cell image disclosed in the embodiment of the present disclosure. As illustrated in FIG. 8A, the grayscale values of the background region and the cell region in the cell image are different. The cell image analysis apparatus may determine the cell region in the cell image in FIG. 8A according to the grayscale threshold segmentation. By performing the grayscale threshold segmentation on the image in FIG. 8A, a cell image processed by grayscale threshold segmentation as illustrated in FIG. 8B is obtained. The cell image processed by the grayscale threshold segmentation as illustrated in FIG. 8B includes the cell region. By performing S component threshold segmentation on the image in FIG. 8B, the image of the red blood cell region including red blood cells and cytoplasm as illustrated in FIG. 8C and the image of the first region including blood platelets and white blood cell nuclei as illustrated in FIG. 8D are obtained. The multi-connected regions in the image of the red blood cell region including red blood cells and cytoplasm in FIG. 8C are filled to obtain the filled image of the red blood cell region including red blood cells and cytoplasm as illustrated in FIG. 8E. The number of red blood cells in the red blood cell region can be obtained by counting the single-connected region whose area meets certain conditions (for example, the area is in the preset area threshold interval) in FIG. 8E. The blood platelets and white blood cell nuclei in FIG. 8D are distinguished according to the area of the connected region to obtain the image of the blood platelet region including blood platelets as illustrated in FIG. 8F. The number of blood platelets in the blood platelet region can be obtained by counting the connected regions (for example, eight-connected regions or four-connected regions) in FIG. 8F. The cell image analysis apparatus acquires the number of red blood cells in the blood sample to be tested, and calculates the number of blood platelets in the blood sample to be tested based on the number of blood platelets and the number of red blood cells in the cell image, and the number of red blood cells in the blood sample to be tested. The above identification process may only be data processing procedure, and intermediate images such as FIG. 8B-FIG. 8F may not be formed, as long as the cell analysis apparatus can identify blood platelets, red blood cells, and white blood cells (optionally) in the cell image.

In the embodiments of the present disclosure, the number of blood platelets in the blood sample to be tested can be accurately calculated. Compared with the manual counting method, there is no need for inspectors to count blood platelets under the microscope for a long time, the blood platelet counting efficiency is improved, while manual errors are avoided.

Figure 9:
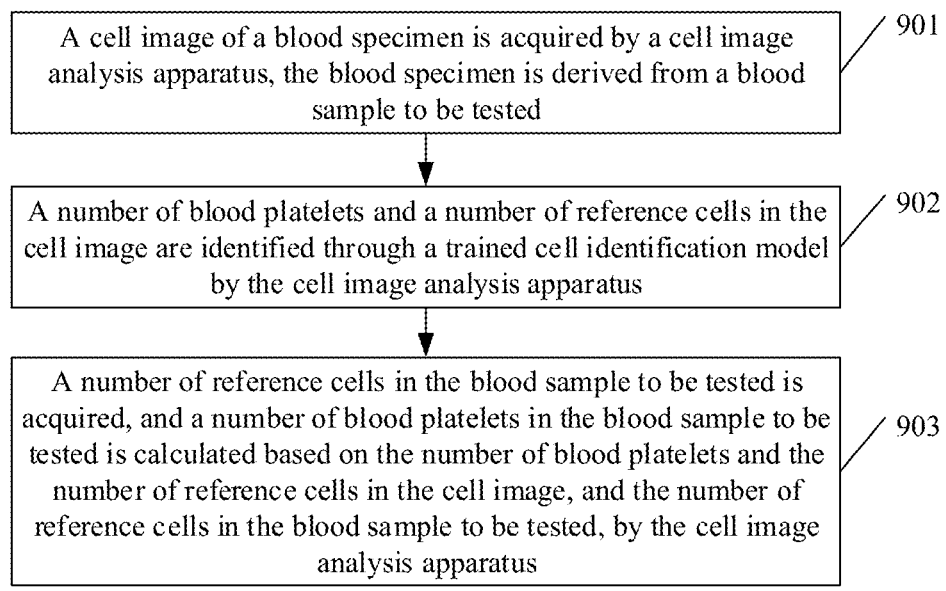
FIG. 9 illustrates a schematic flowchart of another target cell statistical method disclosed in an embodiment of the present disclosure.

With reference to FIG. 9, FIG. 9 illustrates a schematic flowchart of another target cell statistical method disclosed in an embodiment of the present disclosure. FIG. 9 is obtained by further optimization on the basis of FIG. 5. The method illustrated in FIG. 9 may be applied to the cell image analysis apparatus in the specimen analysis system illustrated in FIG. 1. The method includes the following steps.

In 901, a cell image of a blood specimen is acquired by a cell image analysis apparatus. The blood specimen is derived from a blood sample to be tested.

As for the specific implementation of step 901, reference may be made to step 501 as illustrated in FIG. 5, which will not be repeated herein.

In 902, a number of blood platelets and a number of reference cells in the cell image are identified through a trained cell identification model by the cell image analysis apparatus.

In the embodiment of the present disclosure, the cell identification model is a deep neural network model. The trained cell identification model is a qualified cell identification model that is obtained by deep learning network training. It is configured to identify blood platelets and reference cells in the cell image and count the number of blood platelets and the number of reference cells in the cell image.

In the embodiments of the present application, during the detection of the number of blood platelets and the number of red blood cells, a deep neural network may be used to automatically identify and count. Compared with an ordinary artificial neural network, the deep neural network includes a plurality of hidden layers, which automatically learn from a large number of specimens and discover distributed characteristic representations of data. The advantage of adopting a deep neural network is that it automatically learns and mines data characteristics without manually extracting classification characteristics, and higher identification accuracy can be obtained.

The trained cell identification model is obtained by training the cell identification model through a training data set.

The training data set includes a cell picture for training, and the cell picture for training includes labeled target cells and labeled reference cells. Optionally, the target cells may be blood platelets. Optionally, the reference cells may be red blood cells, white blood cells, or red blood cells and white blood cells.

Optionally, before performing step 902, the following steps may also be performed.

(41) The training data set is acquired. The training data set includes a cell picture for training, and the cell picture for training includes labeled target cells and labeled reference cells.

(42) The cell identification model is trained based on the training data set to obtain the trained cell identification model.

Step (41) and step (42) may be performed by a server, or may be performed by the cell image analysis apparatus.

Optionally, the cell identification model includes an input layer, at least one hidden layer and an output layer. Step (42) may specifically include the following steps.

(421) The cell picture for training is input into the input layer and an output result of the cell picture for training is obtained from the output layer.

(422) The trained cell identification model is obtained, in the case where the training amount of the cell identification model reaches a preset training amount threshold, and/or the loss function value of the cell identification model is less than a preset value.

Optionally, step 902 may specifically include the following step.

The cell image analysis apparatus inputs the cell image into the trained cell identification model to obtain the number of blood platelets and the number of reference cells in the cell image.

In the embodiments of the present disclosure, since the cell identification model is obtained by training with a deep learning neural network, there is no need to perform characteristic extraction from the input cell image, and data characteristics can be automatically learned and mined, and a higher identification accuracy can be obtained.

Figure 10:
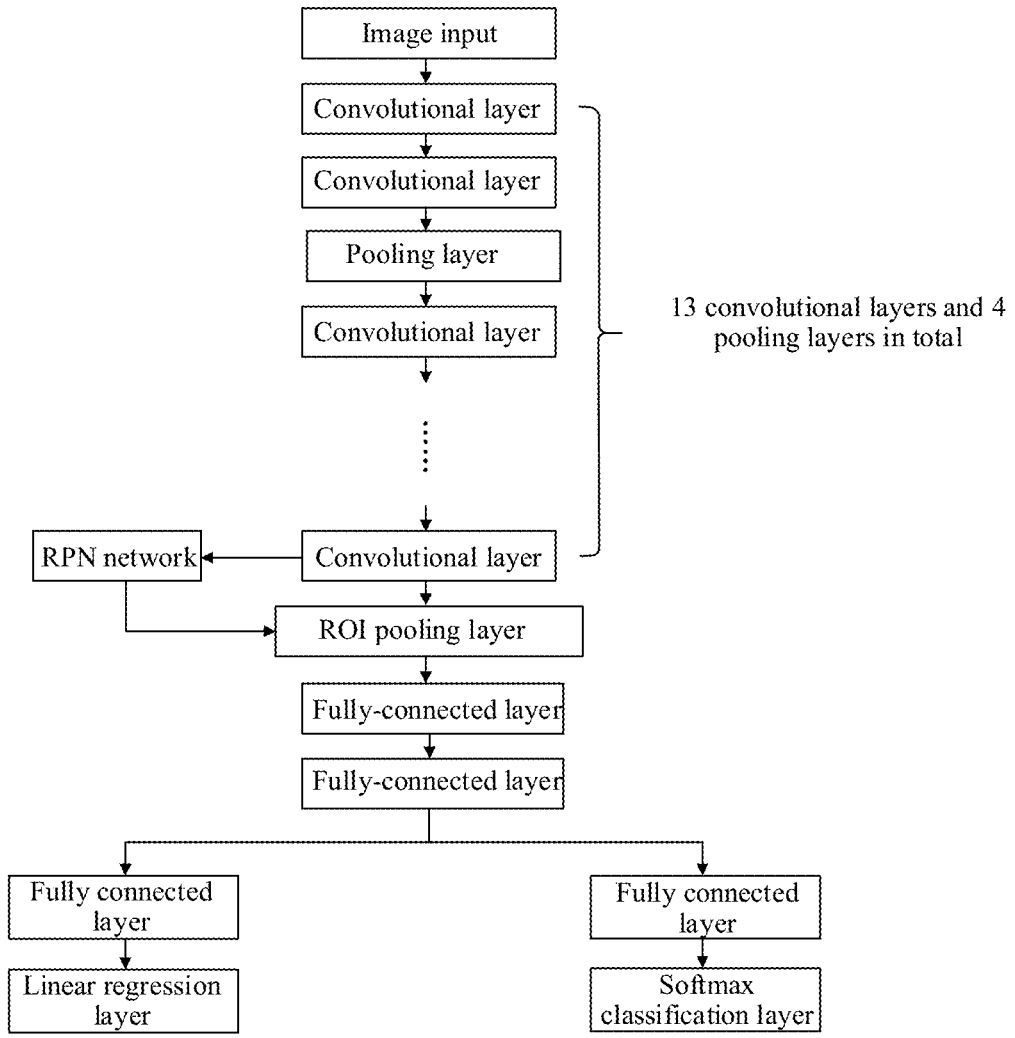
FIG. 10 illustrates a schematic structure diagram of a deep neural network disclosed in an embodiment of the present disclosure.

Faster region convolutional neural networks (Faster R-CNN) may be used as the specific deep neural network model. FIG. 10 illustrates the framework of the Faster R-CNN network structure. The network includes 13 convolutional layers, 4 pooling layers, 1 ROI pooling layer, 1 RPN network, 4 fully connected layers, 1 linear regression layer and 1 softmax classification layer. After the image is input, a plurality of convolution layers and pooling layers are used to automatically generate characteristic maps. Then, the recommended candidate regions, that is, the detected cell regions, are generated through the region proposal network (RPN). The information of these regions is transmitted to the pooling layer of the region of interest (ROI). Each region is reduced to the same size. Then, the information of the regions with the same size is transmitted to the fully connected layer. Finally, the softmax classification layer is used to determine the cell type of these regions, and at the same time, the linear regression layer is used to correct the position of the cells in the region.

The network model may also be modified, such as increasing the number of convolutional layers and pooling layers, that is, increasing the network depth. Other region convolutional neural networks (R-CNN) models such as R-CNN, Fast R-CNN, Mask R-CNN may be used. You only look once (YOLO) model and Single Shot MultiBox Detector (SSD) model may also be used.

Deep neural network requires a large number of labeled specimens for network training, in order to optimize the weights of each neuron in the network to achieve the best network performance. The training of the network can use the gradient descent method. According to the error between the predicted output and the actual result of the current network, the weights of all neurons are continuously adjusted, such that the error between the predicted output and the actual result of the network is minimized finally.

Figure 11:
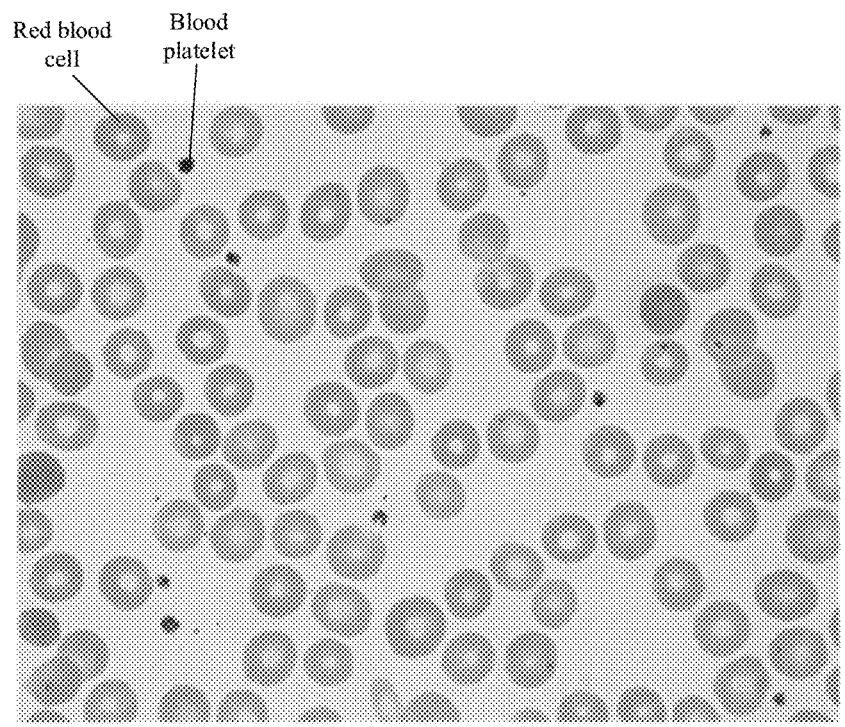
FIG. 11 illustrates an original image of a training specimen disclosed in an embodiment of the present disclosure.
Figure 12:
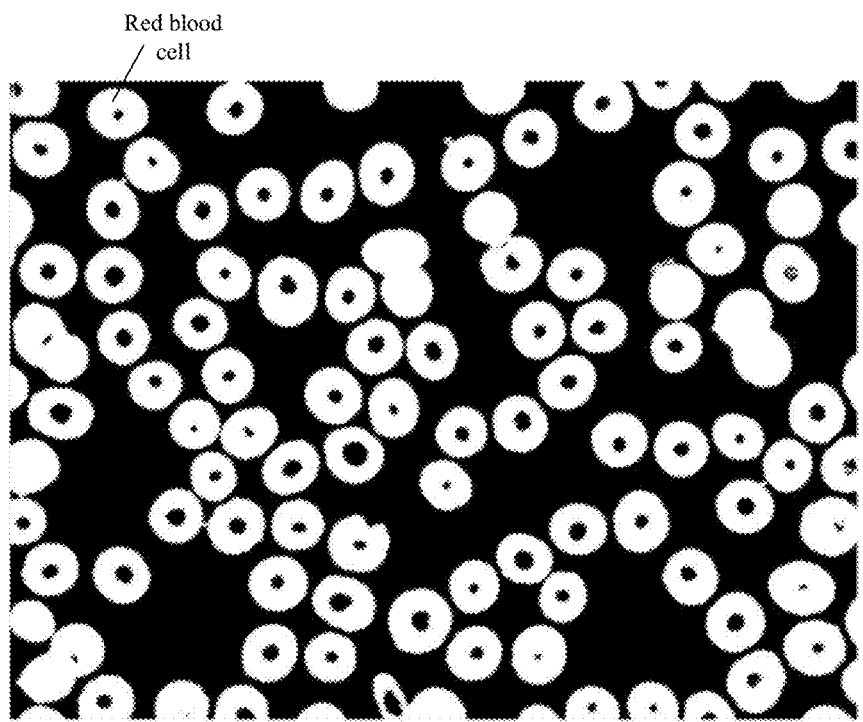
FIG. 12 illustrates a red blood cell labeled image of a training specimen disclosed in an embodiment of the present disclosure.
Figure 13:
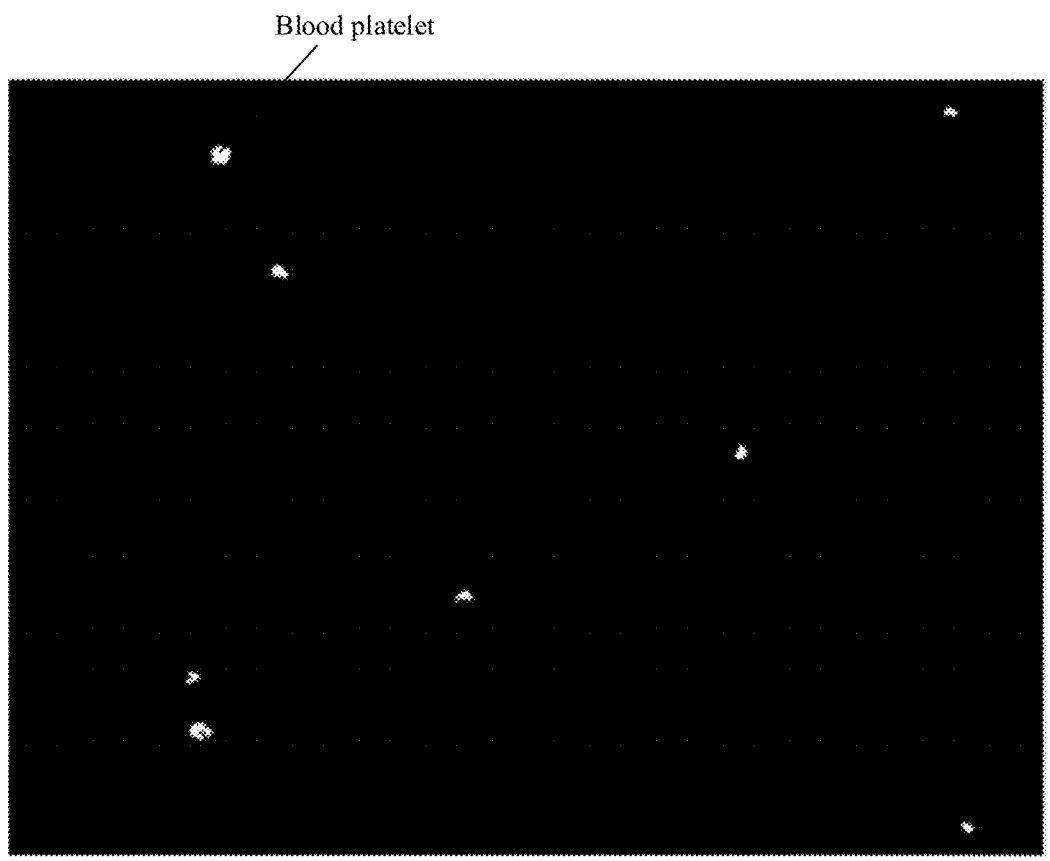
FIG. 13 illustrates a blood platelet labeled image of a training specimen disclosed in an embodiment of the present disclosure.
Figure 14:
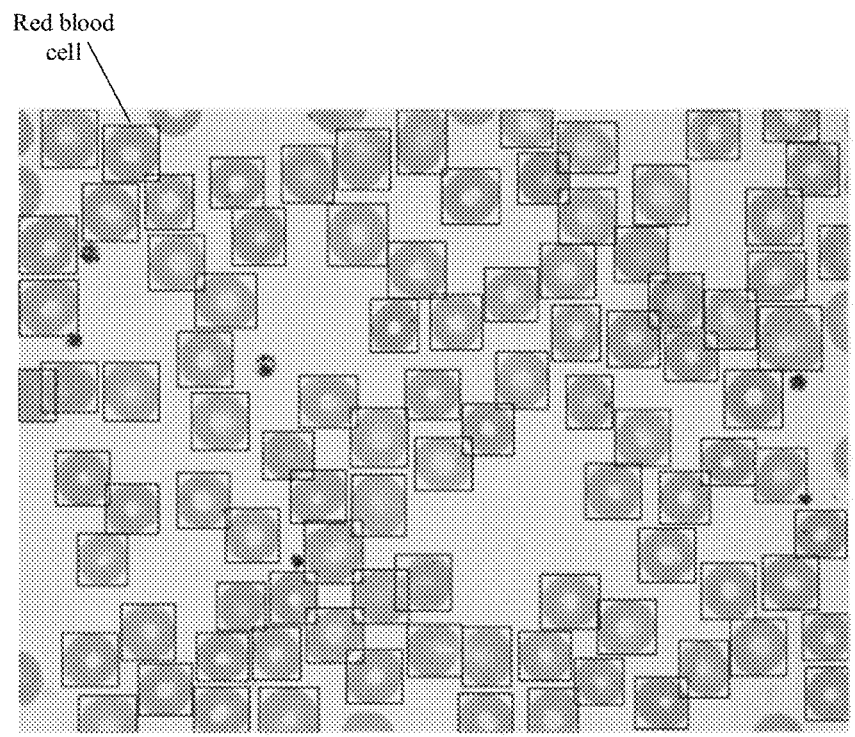
FIG. 14 illustrates a red blood cell labeled image identified by a deep neural network disclosed in an embodiment of the present disclosure.
Figure 15:
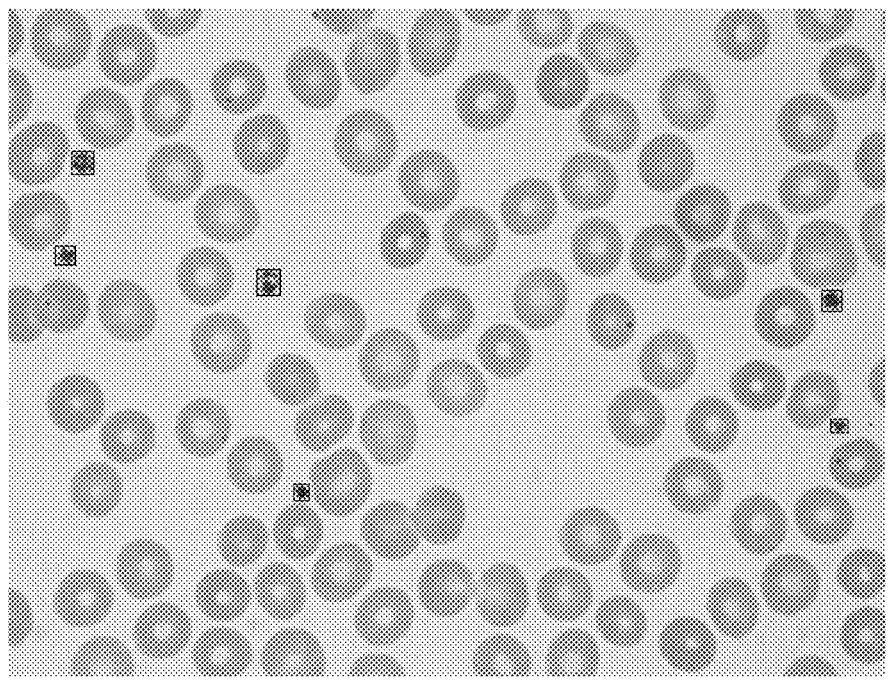
FIG. 15 illustrates a blood platelet labeled image identified by a deep neural network disclosed in an embodiment of the present disclosure.

In the embodiments of the present disclosure, the deep neural network is trained by using pictures in which red blood cells and blood platelets have been labeled. The original image of the training specimen is illustrated in FIG. 11, which includes a large number of red blood cells and a small number of blood platelets that have been clearly labeled. FIG. 12 shows which cells in the specimen are red blood cells, and FIG. 13 shows which cells in the specimen are blood platelets. Deep neural networks are trained by a large number of such labeled specimens, resulting in a network suitable for identifying red blood cells and blood platelets. By inputting the specimen to be tested into the deep neural network, red blood cells and blood platelets can be identified and counted. FIG. 14 shows the red blood cells identified by the deep neural network, which have been marked with rectangular boxes. FIG. 15 shows the blood platelets identified by the deep neural network, which have been marked with rectangular boxes.

In 903, a number of reference cells in the blood sample to be tested is acquired, and a number of blood platelets in the blood sample to be tested is calculated based on the number of blood platelets and the number of reference cells in the cell image, and the number of reference cells in the blood sample to be tested, by the cell image analysis apparatus.

As for the specific implementation of step 903, reference may be made to step 503 illustrated in FIG. 5, which will not be repeated herein.

In the embodiments of the present disclosure, the trained cell identification model may be used to accurately calculate the number of blood platelets in the blood sample to be tested. Compared with the manual counting method, there is no need for inspectors to count blood platelets under the microscope for a long time, the blood platelet counting efficiency is improved, while manual errors are avoided.

It should be noted that, even if target cells aggregate in the blood sample of the present disclosure, the target cell statistical method of the present disclosure can be used to accurately identify and count the blood platelets in the blood sample.

An example in which blood platelets aggregate is provided below. The example will be described with reference to FIG. 16A, FIG. 16B, FIG. 16C, and FIG. 16D.

Figure 16A:
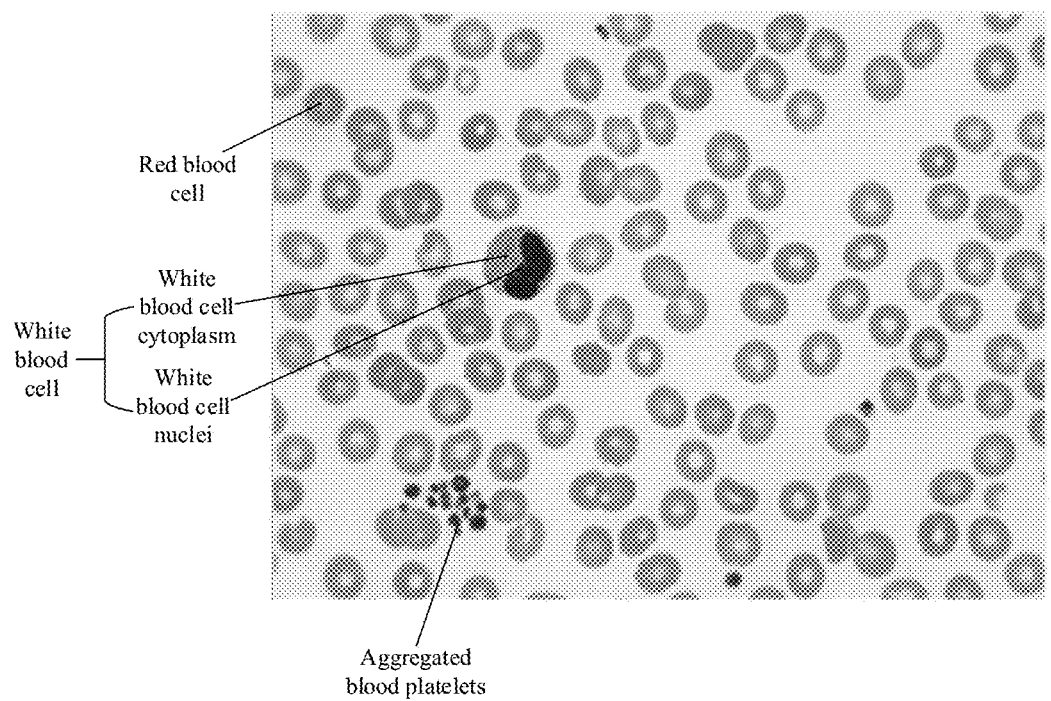
FIG. 16A illustrates a schematic diagram of another cell image disclosed in an embodiment of the present disclosure.
Figure 16B:
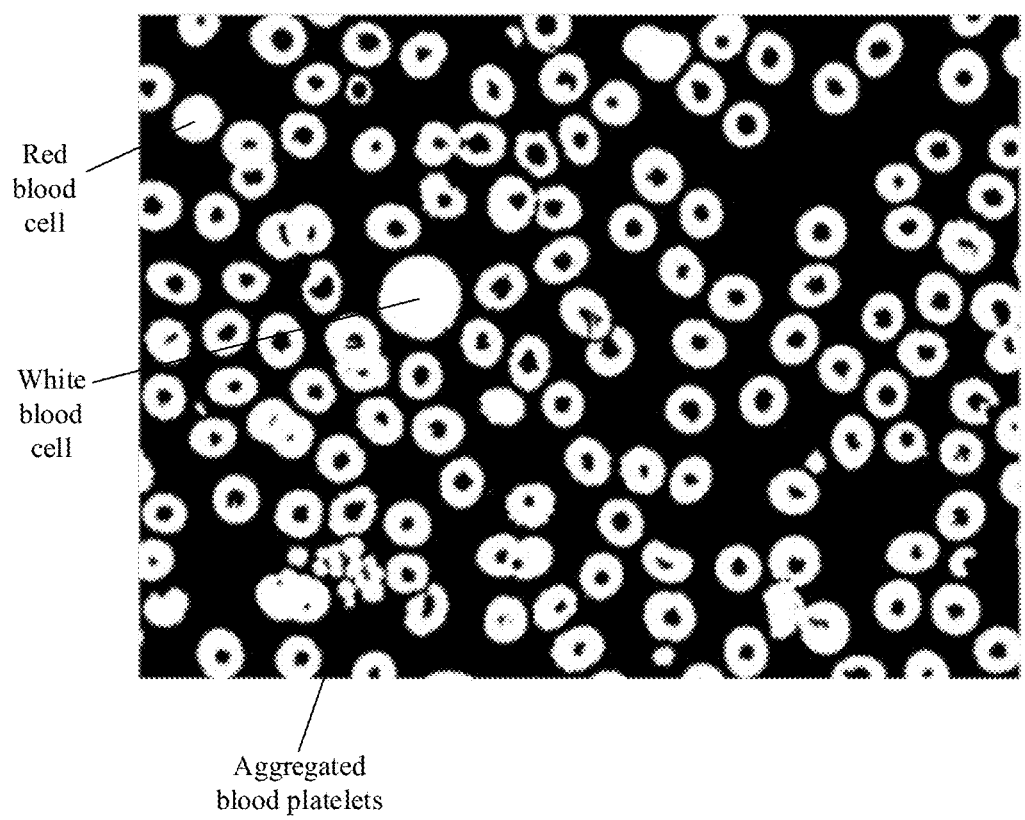
FIG. 16B illustrates another cell image processed by grayscale threshold segmentation disclosed in an embodiment of the present disclosure.
Figure 16C:
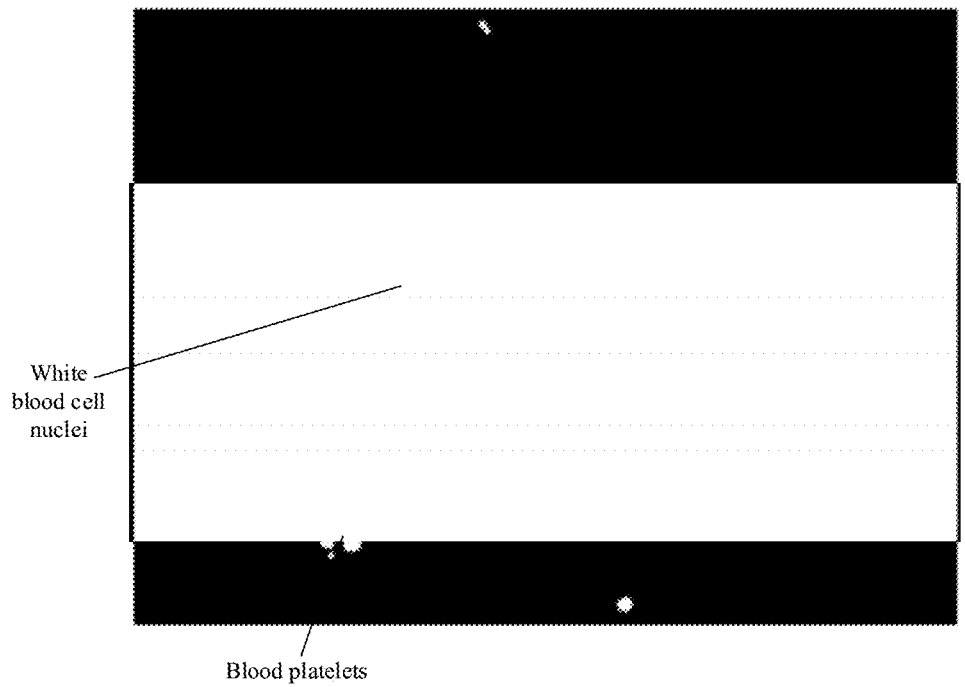
FIG. 16C illustrates an image including white blood cell nuclei and blood platelets disclosed in an embodiment of the present disclosure.
Figure 16D:
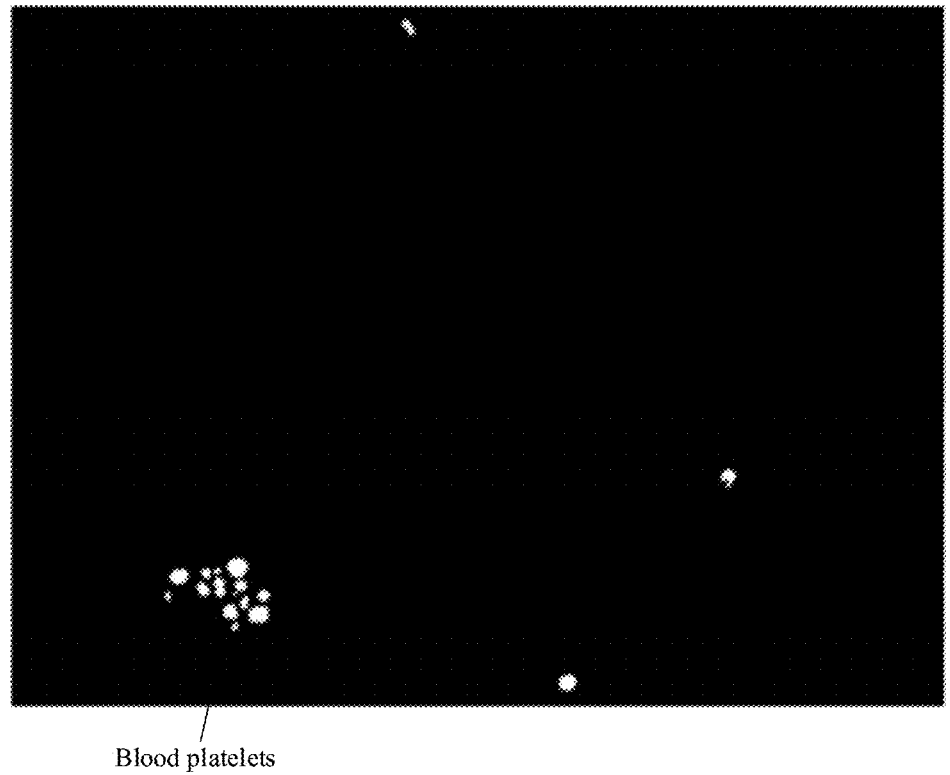
FIG. 16D illustrates an image including blood platelets disclosed in an embodiment of the present disclosure.

With reference to FIG. 16A, FIG. 16A illustrates a schematic diagram of another cell image disclosed in an embodiment of the present disclosure. As illustrated in FIG. 16A, red blood cells, white blood cells (white blood cells including white blood cell nuclei and white blood cell cytoplasm) and aggregated blood platelets are present in the cell image. The grayscale values of the background region and the cell region in the cell image are different. The cell image analysis apparatus may determine the cell region in the cell image in FIG. 16A according to the grayscale threshold segmentation. The image in FIG. 16A is processed by the grayscale threshold segmentation to obtain a cell image processed by the grayscale threshold segmentation as illustrated in FIG. 16B. The cell region is included in the cell image processed the grayscale threshold segmentation as illustrated in FIG. 16B. The image in FIG. 16B is processed by S component threshold segmentation, to obtain the image including white blood cell nuclei and blood platelets as illustrated in FIG. 16C. The image including white blood cell nuclei and blood platelets in FIG. 16C is segmented according to the size of the connected region area to obtain the image including blood platelets as illustrated in FIG. 16D. The number of blood platelets in the cell image can be obtained by counting the connected regions in FIG. 16D. The cell image analysis apparatus acquires the number of red blood cells in the blood sample to be tested, and calculates the number of blood platelets in the blood sample to be tested based on the number of blood platelets and the number of red blood cells in the cell image, and the number of red blood cells in the blood sample to be tested. The above identification process may only be a data processing procedure, and intermediate images such as the images of FIG. 16B-FIG. 16D may not be formed, as long as the cell analysis apparatus can identify blood platelets, red blood cells, and white blood cells (optionally) in the cell image.

In the embodiment of the present disclosure, for the blood sample to be tested with platelet aggregation, the number of blood platelets in the blood sample to be tested can be accurately calculated. Compared with the manual counting method, there is no need for inspectors to count blood platelets under the microscope for a long time, the blood platelet counting efficiency is improved, while manual errors are avoided.

In the above, the solutions in the embodiments of the present disclosure are described from the perspective of the execution process on the method side. It can be understood that, in order to achieve the above functions, the server includes corresponding hardware structures and/or software modules for executing each function. Those skilled in the art would easily appreciate that the present disclosure can be implemented by hardware or in the form of a combination of hardware and computer software, with reference to the illustrative units and algorithm steps described in the embodiments provided herein. A certain function is performed by hardware or computer software driving hardware, depending on the specific application and design constraints of the technical solution. Those skilled in the art may implement the described function by using different methods for each particular application, but such implementations should not be considered beyond the scope of the present disclosure.

In the embodiments of the present disclosure, the server may be divided into functional units according to the above method embodiments. For example, functional units may be divided based on respective functions, or two or more functions may be integrated into one processing unit. The above integrated units may be implemented in the form of hardware, or may be implemented in the form of software functional units. It should be noted that the division of units in the embodiments of the present disclosure is illustrative, which is only a logical function division, and other division methods may be used in actual implementation.

Figure 17:
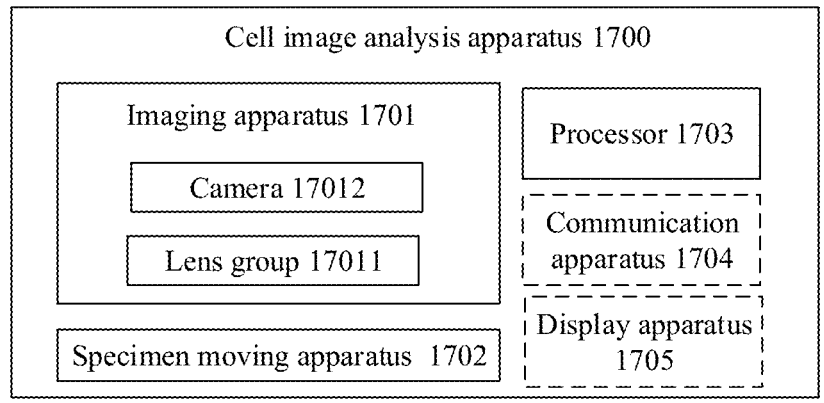
FIG. 17 illustrates a schematic structure diagram of another cell image analysis apparatus disclosed in an embodiment of the present disclosure.

Consistent with the above, reference may be made to FIG. 17. FIG. 17 illustrates a schematic structure diagram of a cell image analysis apparatus disclosed in an embodiment of the present disclosure. The cell image analysis apparatus 1700 includes an imaging apparatus 1701, a specimen moving apparatus 1702 and a processor 1703.

The imaging apparatus 1701 includes a camera 17011 and a lens group 17012. The imaging apparatus is configured to photograph a cell image of a blood specimen derived from the blood sample to be tested.

The specimen moving apparatus 1702 is configured to move the blood specimen relative to the imaging apparatus 1701, so that the imaging apparatus 1701 photographs a cell image of a specific region of the blood specimen.

The processor 1703 is configured to acquire a cell image of the blood specimen, and automatically identify the number of target cells and the number of reference cells in the cell image. The processor is further configured to acquire the number of reference cells in the blood sample to be tested. The processor is further configured to calculate the number of target cells in the blood sample to be tested, based on the number of target cells and the number of reference cells in the cell image, and the number of reference cells in the blood sample to be tested.

Optionally, the movement of the specimen moving apparatus 1702 may be controlled by the processor 1703.

Optionally, the cell image analysis apparatus 1700 further includes a communication apparatus 1704.

Optionally, that the processor 1703 is configured to acquire the number of reference cells in the blood sample to be tested, includes the following.

The processor 1703 controls the communication apparatus 1704 to automatically acquire the number of reference cells in the blood sample to be tested from a blood analyzer.

Optionally, that the processor 1703 is configured to acquire the number of reference cells in the blood sample to be tested, includes the following.

The processor 1703 is configured to receive the number of reference cells in the blood sample to be tested input by the user.

Optionally, the target cells include blood platelets.

Optionally, the target cells are blood platelets.

Optionally, that the processor 1703 is configured to automatically identify the number of blood platelets and the number of reference cells in the cell image, includes the following.

The processor 1703 automatically identifies blood platelets and reference cells in the cell image and counts the number of blood platelets and the number of reference cells, by using an image processing method.

Optionally, the image processing method includes an image segmentation method.

Optionally, that the processor 1703 automatically identifies blood platelets and reference cells in the cell image and counts the number of blood platelets and reference cells by using an image processing method, is specifically as follows.

The processor 1703 identifies a cell region in the cell image based on the characteristic difference between the cells and the background in the cell image by using the image processing method. The processor classifies the cells in the cell region and identifies a blood platelet region and a reference cell region in the cell region based on the characteristic difference between different cells. The processor counts the number of blood platelets in the blood platelet region and the number of reference cells in the reference cell region.

Optionally, that the processor 1703 automatically identifies a cell region in the cell image based on the characteristic difference between the cells and the background in the cell image by using the image processing method, is specifically as follows.

The processor 1703 identifies the cell region in the cell image by performing grayscale processing on the cell image based on the grayscale difference between the cells and the background in the cell image.

Optionally, that the processor 1703 automatically identifies a cell region in the cell image based on the characteristic difference between the cells and the background in the cell image by using the image processing method, is specifically as follows.

The processor 1703 identifies the cell region in the cell image by performing specific color space conversion on the cell image based on the difference in component of the specific color space between the cells and the background in the cell image.

Optionally, the reference cells include one of red blood cells, white blood cells, and a combination of red blood cells and white blood cells.

Optionally, the reference cells include red blood cells.

Optionally, the reference cells are red blood cells.

Optionally, the reference cells are white blood cells.

Optionally, the reference cells are a combination of red blood cells and white blood cells.

Optionally, that the processor 1703 classifies the cells in the cell region and identifies a blood platelet region and a reference cell region in the cell region based on the characteristic difference between different cells, is specifically as follows.

The processor 1703 identifies a red blood cell region and a first region in the cell region based on the difference in component of the specific color space between the red blood cells and a first type of cells in the cell region. The first type of cells includes white blood cells and blood platelets, and the first region includes a white blood cell region (that is, the region of white blood cell nuclei) and the blood platelet region in the cell region. The processor identifies the blood platelet region in the first region or the white blood cell region and blood platelet region in the first region, based on the difference in area between white blood cells and blood platelets in the first region.

The reference cell region includes the red blood cell region when the reference cell includes red blood cells. The reference cell region includes the white blood cell region when the reference cell includes white blood cells. The reference cell region includes the red blood cell region and the white blood cell region when the reference cell includes a combination of red blood cells and white blood cells.

Optionally, that the processor 1703 counts the number of blood platelets in the blood platelet region and the number of reference cells in the reference cell region, is specifically as follows.

The processor 1703 counts the number of blood platelets in the blood platelet region and the number of red blood cells in the red blood cell region, in the case where the reference cell includes red blood cells.

The processor 1703 counts the number of blood platelets in the blood platelet region and the number of corresponding white blood cells in the white blood cell region, in the case where the reference cell includes white blood cells.

The processor 1703 counts the number of blood platelets in the blood platelet region, the number of red blood cells in the red blood cell region, and the number of corresponding white blood cells in the white blood cell region, in the case where the reference cell includes a combination of red blood cells and white blood cells.

Optionally, that the processor 1703 counts the number of blood platelets in the blood platelet region, is specifically as follows.

The processor 1703 counts the number of connected regions in the blood platelet region, and takes the number of connected regions in the blood platelet region as the number of blood platelets in the blood platelet region.

Optionally, that the processor 1703 counts the number of reference cells in the reference cell region, is specifically as follows.

The processor 1703 fills holes in a multi-connected region in the red blood cell region, and determines the number of reference cells in the reference cell region according to the parameter of a single-connected region in the red blood cell region, in the case where the reference cell includes red blood cells.

The processor 1703 counts the number of connected regions in the white blood cell region, and takes the number of connected regions in the white blood cell region as the number of reference cells in the reference cell region, in the case where the reference cell includes white blood cells.

The processor 1703 counts the number of connected regions in the white blood cell region, and determines the number of white blood cells in the reference cell region according to the number of connected regions in the white blood cell region. The processor fills holes in the multi-connected region in the red blood cell region, and determines the number of red blood cells in the reference cell region according to the parameter of the single-connected region in the red blood cell region. The sum of the number of white blood cells in the reference cell region and the number of red blood cells in the reference cell region is used as the number of reference cells in the reference cell region, in the case where the reference cell includes a combination of red blood cells and white blood cells.

The connected region in the blood platelet region and the connected region in the white blood cell region include an eight-connected region or a four-connected region.

Optionally, the parameter of the single-connected region includes the number of single-connected regions. That the processor 1703 determines the number of reference cells in the reference cell region according to the parameter of the single-connected region in the red blood cell region, is specifically as follows.

The processor 1703 counts the number of single-connected regions in the red blood cell region, and takes the number of single-connected regions in the red blood cell region as the number of reference cells in the reference cell region.

That the processor 1703 determines the number of red blood cells in the reference cell region according to the parameter of the single-connected region in the red blood cell region, is specifically as follows.

The processor 1703 counts the number of single-connected regions in the red blood cell region, and takes the number of single-connected regions in the red blood cell region as the number of red blood cells in the reference cell region.

Optionally, the parameter of the single-connected region includes the number of single-connected regions and the area of the single-connected regions. The processor 1703 determines the number of reference cells in the reference cell region according to the parameter of the single-connected region in the red blood cell region, is specifically as follows.

The processor 1703 counts the number of single-connected regions with an area in a preset area threshold interval in the red blood cell region, and takes the number of single-connected regions with an area in a preset area threshold interval in the red blood cell region as the number of reference cells in the reference cell region.

That the processor 1703 determines the number of red blood cells in the reference cell region according to the parameter of the single-connected region in the red blood cell region, is specifically as follows.

The processor 1703 counts the number of single-connected regions with an area in a preset area threshold interval in the red blood cell region, and takes the number of single-connected regions with an area in a preset area threshold interval in the red blood cell region as the number of red blood cells in the reference cell region.

Optionally, the specific color space includes one of RGB color space, HSV color space, HSI color space, Lab color space, YUV color space or YCbCr color space.

Optionally, the component of the specific color space includes any component in RGB color space or any component in HSV color space or any component in HSI color space or any component in Lab color space or any component in YUV color space or any component in YCbCr color space.

Optionally, the image processing method includes a deep learning method.

Optionally, that the processor 1703 identifies blood platelets and reference cells in the cell image, and counts the number of blood platelets and the number of reference cells by using an image processing method, is specifically as follows.

The processor 1703 identifies the number of blood platelets and the number of reference cells in the cell image through the trained cell identification model.

Optionally, the trained cell identification model is obtained by training the cell identification model through a training data set.

The training data set includes a cell picture for training, and the cell picture for training includes labeled target cells and labeled reference cells.

Optionally, the cell identification model includes an input layer, at least one hidden layer and an output layer. The processor 1703 is configured as follows.

The processor 1703 is configured to input the cell picture for training into the input layer, and obtain an output result of the cell picture for training from the output layer.

The processor 1703 is configured to determine that the trained cell identification model is obtained, in the case where the training amount of the cell identification model reaches a preset training amount threshold, and/or the loss function value of the cell identification model is less than a preset value.

Optionally, that the processor 1703 identifies the number of blood platelets and the number of reference cells in the cell image through the trained cell identification model, is specifically as follows.

The processor 1703 inputs the cell image into the trained cell identification model to obtain the number of blood platelets and the number of reference cells in the cell image.

Optionally, that the processor 1703 calculates the number of target cells in the blood sample to be tested based on the number of target cells and the number of reference cells in the cell image and the number of reference cells in the blood sample to be tested, is specifically as follows.

The processor 1703 calculates the number of target cells in the blood sample to be tested according to the following formula:

$$N_{PLT} = \frac{M_{PLT}}{M_{RFBC}} \cdot N_{RFBC}$$

In the formula, $N_{PLT}$ is the number of target cells in the blood sample to be tested, $N_{RFBC}$ is the number of reference cells in the blood sample to be tested, $M_{PLT}$ is the number of target cells in the cell image, and $M_{RFBC}$ is the number of reference cells in the cell image.

Optionally, that the processor 1703 acquires a cell image of a blood specimen, is specifically as follows.

The processor 1703 acquires a cell image of the blood specimen photographed by a photographing apparatus. Alternatively, the processor 1703 acquires an input cell image of the blood specimen.

Optionally, the blood specimen is prepared into a blood smear. That the processor 1703 acquires a cell image of the blood specimen photographed by a photographing apparatus, is specifically as follows.

The processor 1703 acquires a cell image of a specific region of the blood smear photographed by the photographing apparatus. The specific region includes at least one of a body-tail junction region, a body region, an edge region at either side, or a tail region of the blood smear.

Optionally, the blood specimen is prepared into a blood smear. That the processor 1703 acquires a cell image of the blood specimen photographed by a photographing apparatus, is specifically as follows.

The processor 1703 acquires at least two cell pictures of a specific region of the blood smear photographed by the photographing apparatus. The specific region includes at least one of a body-tail junction region, a body region, an edge region at either side, or a tail region of the blood smear.

The processor 1703 combines the at least two cell pictures into a cell image, and the cell image includes the at least two cell pictures or the cell image is formed by splicing the at least two cell pictures.

Optionally, the at least two pictures (which may be directly used as the cell images) obtained may also be cell images of a blood specimen input by other devices or users and received by the processor, as described above, which is not limited herein.

Optionally, after the processor 1703 automatically identifies the number of target cells and the number of reference cells in the cell image, the processor 1703 is configured as follows.

The processor 1703 is configured to acquire the number of reference cells in the blood sample to be tested, and calculate the number of target cells in the blood sample to be tested based on the number of target cells and the number of reference cells in the cell image and the number of reference cells in the blood sample to be tested, in the case where the number of reference cells is greater than or equal to a first threshold.

Optionally, the processor 1703 is configured as follows.

The processor 1703 is configured to acquire a cell image of the blood specimen, in the case where the number of reference cells is less than the first threshold.

Optionally, after the processor 1703 automatically identifies the number of target cells and the number of reference cells in the cell image, the processor 1703 is configured as follows.

The processor 1703 is configured to determine whether a sum of the numbers of reference cells in all cell images of the blood specimen acquired in history is greater than or equal to a second threshold.

That the processor 1703 acquires the number of reference cells in the blood sample to be tested, and calculates the number of target cells in the blood sample to be tested based on the number of target cells and the number of reference cells in the cell image and the number of reference cells in the blood sample to be tested, is specifically as follows.

The processor 1703 acquires the number of reference cells in the blood sample to be tested, and calculates the number of target cells in the blood sample to be tested based on the sum of the numbers of reference cells in all cell images of the blood specimen, the sum of the numbers of target cells in all cell images of the blood specimen, and the number of reference cells in the blood sample to be tested, in the case where the sum of the numbers of reference cells in all cell images of the blood specimen acquired in history is greater than or equal to the second threshold.

Optionally, the processor 1703 is configured as follows.

The processor 1703 is configured to acquire a cell image of the blood specimen, in the case where the sum of the numbers of reference cells in all cell images of the blood specimen acquired in history is less than the second threshold.

Optionally, the processor may also simultaneously acquire at least two cell images of the blood specimen, automatically identify the at least two cell images of the blood specimen, and obtain the number (sum) of the reference cells and/or the number (sum) of the target cells in the at least two cell images, and then determine whether the number (sum) of the reference cells obtained in the cell images of the blood specimen is greater than or equal to the first threshold (or the second threshold). For subsequent steps, reference may be made to those described above. The accuracy of the test results can be ensured while the efficiency is improved.

Optionally, the cell image analysis apparatus further includes a display apparatus 1705.

The display apparatus 1705 is configured to display the number of target cells in the blood sample to be tested.

Optionally, the processor 1703 controls the communication apparatus 1704 to transmit the number of target cells in the blood sample to be tested to other devices for display.

Optionally, the other devices include one of a blood analyzer, a blood smear preparation apparatus, or a terminal device.

For the specific implementation of the cell image analysis apparatus in the embodiments of the present disclosure, reference may be made to the method embodiments illustrated in FIG. 5 to FIG. 9, which will not be repeated herein.

In the embodiments of the present disclosure, the cell image analysis apparatus may automatically identify the number of target cells and the number of reference cells in the cell image of the blood specimen, and calculate the number of target cells in the blood sample to be tested, based on the number of target cells and the number of reference cells in the cell image, and the number of reference cells in the blood sample to be tested. The number of target cells in the blood sample to be tested can be accurately calculated. Compared with the manual counting method, the inspector does not need to count the target cells under the microscope for a long time, the counting efficiency of the target cells is improved, while manual errors are avoided.

Figure 18:
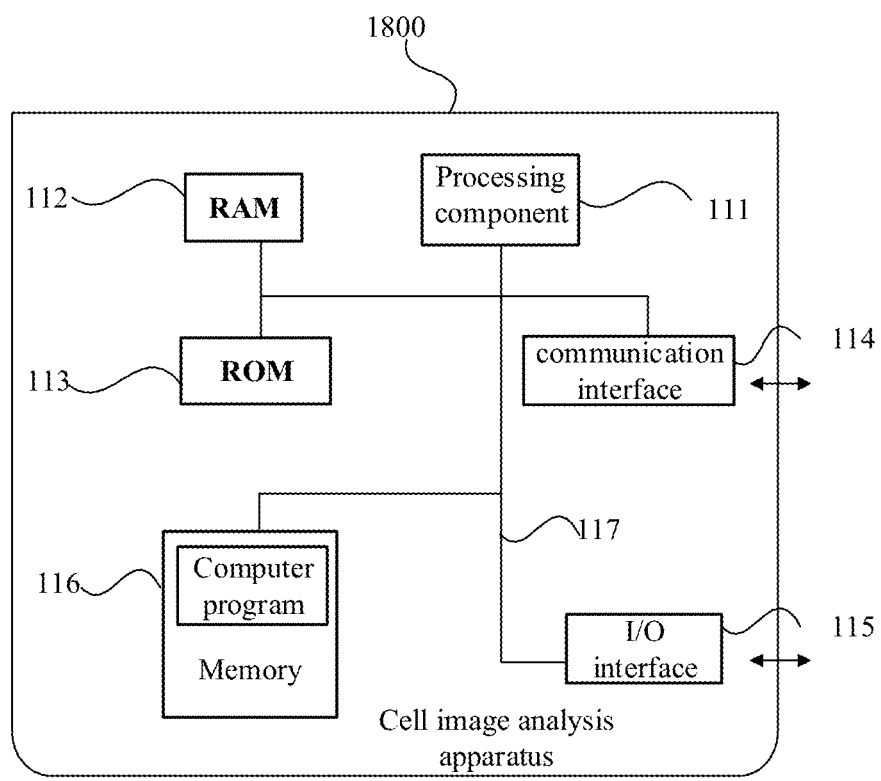
FIG. 18 illustrates a schematic structure diagram of another cell image analysis apparatus disclosed in an embodiment of the present disclosure.

With reference to FIG. 18, FIG. 18 illustrates a schematic structure diagram of a cell image analysis apparatus disclosed in an embodiment of the present disclosure. As illustrated in FIG. 18, the cell image analysis apparatus 1800 at least includes: a processing component 111, a random access memory (RAM) 112, a read-only memory (ROM) 113, a communication interface 114, a memory 116 and an I/O interface 115. The processing component 111, the RAM 112, the ROM 113, the communication interface 114, the memory 116 and the I/O interface 115 communicate via bus 117.

The processing component 111 may be a central processing unit (CPU), a graphics processing unit (GPU) or other chips with computing capabilities.

The memory 116 contains various computer programs, such as an operating system and an application program, which may be executed by the processing component 111, and data necessary for the execution of the computer programs. In addition, during the detection of the blood sample to be tested, if there are data which need to be stored locally, the data can be stored in the memory 116. The computer program includes program instructions, and the processor 1901 is configured to invoke the program instructions to execute the method steps performed by the cell image analysis apparatus shown in FIG. 5-FIG. 9.

The I/O interface 115 is composed of a serial interface such as universal serial bus (USB), institute of electrical and electronics engineers (IEEE) 1394 or recommended standard RS-232C, a parallel interface such as a small computer system interface (SCSI), integrated drive electronics (IDE) interface or IEEE 1284, and an analog signal interface composed of a digital/analog (D/A) converter, an analog/digital (A/D) converter, and the like. An input device composed of a keyboard, a mouse, a touch screen or other control buttons is connected to the I/O interface 115, and a user can directly input data to the data processing apparatus 50 by using the input device. In addition, the I/O interface 115 can also be connected to a displayer with a displaying function, such as a liquid crystal screen, a touch screen, an LED display screen, an OLED display screen, etc. The data processing apparatus 50 can output the processed data as image display data to the displayer for display, for example, analysis data, instrument operating parameters, etc.

Communication interface 114 may be an interface of any communication protocol known currently. The communication interface 114 communicates with the outside world through a network. Through the communication interface 114, the cell image analysis apparatus 1900 can transmit data to any apparatus connected to the network with a certain communication protocol.

In the embodiments of the present disclosure, the cell image analysis apparatus may automatically identify the number of target cells and the number of reference cells in the cell image of the blood specimen, and calculates the number of target cells in the blood sample to be tested, based on the number of target cells and the number of reference cells in the cell image, and the number of reference cells in the blood sample to be tested. The number of target cells in the blood sample to be tested can be accurately calculated. Compared with the manual counting method, the inspector does not need to count the target cells under the microscope for a long time, the counting efficiency of the target cells is improved, while manual errors are avoided.

The embodiments of the present disclosure further provide a computer storage medium. The computer storage medium stores a computer program for electronic data exchange. The computer program enables the computer to execute some or all of the steps in any one of the target cell statistical methods described in the above method embodiments.

The embodiments of the present disclosure further provide a computer program product. The computer program product includes a non-transitory computer-readable storage medium storing a computer program. The computer program enables the computer to execute some or all of the steps in any one of the target cell statistical methods described in the above method embodiments.

It should be noted that, for the sake of brief description, the above method embodiments are all described as combinations of a series of actions. However, those skilled in the art should understand that the present disclosure is not limited by the described action sequence, since certain steps may be performed in other orders or simultaneously according to the present disclosure. In addition, those skilled in the art should also understand that the embodiments described in the specification are all preferred embodiments, and the actions and modules involved are not necessarily required by the present disclosure.

In the above embodiments, the description of each embodiment has its own emphasis. For parts that are not described in detail in a certain embodiment, reference may be made to the relevant descriptions of other embodiments.

In the several embodiments provided in the present disclosure, it should be understood that the disclosed apparatus may be implemented in other manners. For example, the apparatus embodiments described above are only illustrative. For example, the division of the units is only a logical function division, and there may be other division methods in actual implementation. For example, a plurality of units or components may be combined or integrated into another system, or some characteristics can be ignored, or are not implemented. On the other hand, the shown or discussed mutual coupling or direct coupling or communication connection may be indirect coupling or communication connection of apparatus or units through some interfaces, and may be electrically or others.

The units described as separate components may be or may not be physically separated. The components shown as units may be or may not be physical units, that is, they may be located in a place, or may be distributed to a plurality of network units. Some or all of the units may be selected according to actual needs to achieve the purpose of the solution in a certain embodiment.

In addition, each functional unit in each embodiment of the present disclosure may be integrated into one processing unit, or each unit may be physically separate, or two or more units may be integrated into one unit. The above integrated units can be implemented in the form of hardware, or can be implemented in the form of software program modules.

If the integrated unit is implemented in the form of a software program module and sold or used as a stand-alone product, it may be stored in a computer readable memory. Based on this understanding, the technical solution of the present disclosure, or the part that contributes to the prior art, or all or part of the technical solution, can be embodied in the form of a software product in essence. The computer software product is stored in a memory, and includes instructions for enabling a computer device (which may be a personal computer, a server, or a network device, etc.) to execute all or part of the steps of the methods described in the embodiments of the present disclosure. The above memory includes a U disk, a read-only memory (ROM), a random access memory (RAM), a mobile hard disk, a magnetic disk, or an optical disk and other media that can store program codes.

Those of ordinary skill in the art would understand that all or part of the steps in the various methods of the above embodiments can be performed by a program for instructing relevant hardware. The program can be stored in a computer-readable memory. The memory can include a flash disk, a read-only memory, a random access memory, a magnetic disk or an optical disk, etc.

The embodiments of the present disclosure are described in detail above.

Specific examples are used in the specification to illustrate the principles and implementations of the present disclosure. The description of the above embodiments is only used to understand the methods and core ideas of the present disclosure. Moreover, for those of ordinary skill in the art, according to the concept of the present disclosure, modifications may be made in the specific embodiments and application scope. To sum up, the contents of this specification should not be construed as limitations to the present disclosure.

The invention claimed is:

1. A target cell statistical method, comprising:
   acquiring a cell image of a blood specimen by a cell image analysis apparatus, wherein the blood specimen is derived from a blood sample to be tested;
   automatically identifying a number of target cells and a number of reference cells in the cell image by the cell image analysis apparatus; and
   automatically acquiring, by the cell image analysis apparatus, a number of reference cells in the blood sample to be tested from a blood analyzer, and calculating, by the cell image analysis apparatus, a number of target cells in the blood sample to be tested based on the number of target cells and the number of reference cells in the cell image and the number of reference cells in the blood sample to be tested.

2. The method according to claim 1, wherein the target cells comprise blood platelets, white blood cells, or red blood cells;
   wherein the reference cells comprise red blood cells, white blood cells, or a combination thereof; and
   wherein the target cells and the reference cells are different in type.

3. The method according to claim 1, wherein the target cells are blood platelets, and wherein automatically identifying a number of target cells and a number of reference cells in the cell image by the cell image analysis apparatus comprises:
   identifying a cell region in the cell image based on a characteristic difference between cells and background in the cell image by the cell image analysis apparatus using an image processing method;
   classifying cells in the cell region and identifying a blood platelet region and a reference cell region in the cell region based on a characteristic difference between different cells by the cell image analysis apparatus; and
   counting a number of blood platelets in the blood platelet region and a number of reference cells in the reference cell region as the number of target cells and the number of reference cells respectively by the cell image analysis apparatus.

4. The method according to claim 3, wherein identifying a cell region in the cell image based on a characteristic difference between cells and background in the cell image by the cell image analysis apparatus using an image processing method comprises:
   identifying the cell region in the cell image by performing grayscale processing on the cell image based on a grayscale difference between the cells and the background in the cell image by the cell image analysis apparatus;
   or
   identifying the cell region in the cell image by performing specific color space conversion on the cell image based on a difference in a component of specific color space between the cells and the background in the cell image by the cell image analysis apparatus; wherein the component of specific color space comprises any component in RGB color space, or any component in HSV color space, or any component in HSI color space, or any component in Lab color space, or any component in YUV color space, or any component in YCbCr color space.

5. The method according to claim 3, wherein classifying cells in the cell region and identifying a blood platelet region and a reference cell region in the cell region based on a characteristic difference between different cells by the cell image analysis apparatus comprises:
   identifying a red blood cell region and a first region in the cell region based on a difference in a component of specific color space between red blood cells and a first type of cells in the cell region by the cell image analysis apparatus; wherein the first type of cells comprises white blood cells and blood platelets, and the first region comprises a white blood cell region and the blood platelet region in the cell region; and wherein the component of specific color space comprises any component in RGB color space, or any component in HSV color space, or any component in HSI color space, or any component in Lab color space, or any component in YUV color space, or any component in YCbCr color space; and
   identifying the blood platelet region in the first region or the white blood cell region and the blood platelet region in the first region, based on a difference in an area between white blood cells and blood platelets in the first region by the cell image analysis apparatus;
   wherein the reference cell region comprises the red blood cell region when the reference cells comprise red blood cells; the reference cell region comprises the white blood cell region when the reference cells comprise white blood cells; or the reference cell region comprises the red blood cell region and the white blood cell region when the reference cells comprise a combination of red blood cells and white blood cells; and
   wherein counting a number of blood platelets in the blood platelet region and a number of reference cells in the reference cell region as the number of target cells and the number of reference cells respectively by the cell image analysis apparatus comprises:
   counting the number of blood platelets in the blood platelet region and the number of red blood cells in the red blood cell region by the cell image analysis apparatus, when the reference cells comprise red blood cells;
   counting the number of blood platelets in the blood platelet region and the number of white blood cells in the white blood cell region by the cell image analysis apparatus, when the reference cells comprise white blood cells; or counting the number of blood platelets in the blood platelet region, and the number of red blood cells in the red blood cell region and the number of white blood cells in the white blood cell region by the cell image analysis apparatus, when the reference cells comprise a combination of red blood cells and white blood cells.

6. The method according to claim 5, wherein counting the number of blood platelets in the blood platelet region by the cell image analysis apparatus comprises:
counting a number of connected regions in the blood platelet region, and taking the number of connected regions in the blood platelet region as the number of blood platelets in the blood platelet region by the cell image analysis apparatus; and
wherein counting the number of red blood cells in the red blood cell region by the cell image analysis apparatus comprises:
counting a number of connected regions in the red blood cell region, and taking the number of connected regions in the red blood cell region as the number of reference cells in the reference cell region by the cell image analysis apparatus, when the reference cells comprise red blood cells;
wherein counting the number of white blood cells in the white blood cell region by the cell image analysis apparatus comprises:
counting a number of connected regions in the white blood cell region, and taking the number of connected regions in the white blood cell region as the number of reference cells in the reference cell region by the cell image analysis apparatus, when the reference cells comprise white blood cells; or
wherein counting the number of red blood cells in the red blood cell region and the number of white blood cells in the white blood cell region by the cell image analysis apparatus comprises:
counting a number of connected regions in the red blood cell region and a number of connected regions in the white blood cell region, and taking the number of connected regions in the red blood cell region and the number of connected regions in the white blood cell region as the number of reference cells in the reference cell region by the cell image analysis apparatus, when the reference cells comprise a combination of red blood cells and white blood cells.

7. The method according to claim 1, wherein automatically identifying a number of target cells and a number of reference cells in the cell image by the cell image analysis apparatus comprises:
identifying the number of target cells and the number of reference cells in the cell image through a trained cell identification model by the cell image analysis apparatus;
wherein the trained cell identification model is obtained by training a cell identification model with a training data set; and
wherein the training data set comprises a cell picture for training, and the cell picture for training comprises labeled target cells and labeled reference cells.

8. The method according to claim 1, wherein calculating, by the cell image analysis apparatus, a number of target cells in the blood sample to be tested based on the number of target cells and the number of reference cells in the cell image and the number of reference cells in the blood sample to be tested comprises:
calculating the number of target cells in the blood sample to be tested by the cell image analysis apparatus according to the following formula:

$$N_{PLT} = \frac{M_{PLT}}{M_{RFBC}} \cdot N_{RFBC}$$

wherein $N_{PLT}$ is the number of target cells in the blood sample to be tested, $N_{RFBC}$ is the number of reference cells in the blood sample to be tested, $M_{PLT}$ is the number of target cells in the cell image, and $M_{RFBC}$ is the number of reference cells in the cell image.

9. The method according to claim 1, wherein after automatically identifying the number of target cells and the number of reference cells in the cell image by the cell image analysis apparatus, the method further comprises:
when the number of reference cells in the cell image is greater than or equal to a first threshold, performing the step of acquiring, by the cell image analysis apparatus, the number of reference cells in the blood sample to be tested, and calculating, by the cell image analysis apparatus, the number of target cells in the blood sample to be tested, based on the number of target cells and the number of reference cells in the cell image and the number of reference cells in the blood sample to be tested;
or
when the number of reference cells in the cell image is less than the first threshold, performing again the step of acquiring a cell image of the blood specimen by the cell image analysis apparatus.

10. The method according to claim 1, wherein after automatically identifying the number of target cells and the number of reference cells in the cell image by the cell image analysis apparatus, the method further comprises:
determining whether a sum of the numbers of reference cells in all cell images of the blood specimen acquired in history is greater than or equal to a second threshold by the cell image analysis apparatus;
when the sum of the numbers of reference cells in all cell images of the blood specimen acquired in history is greater than or equal to the second threshold, acquiring, by the cell image analysis apparatus, the number of reference cells in the blood sample to be tested, and calculating, by the cell image analysis apparatus, the number of target cells in the blood sample to be tested based on the sum of the numbers of reference cells in all cell images of the blood specimen, a sum of the numbers of target cells in all cell images of the blood specimen, and the number of reference cells in the blood sample to be tested;
or
when the sum of the numbers of reference cells in all cell images of the blood specimen acquired in history is less than the second threshold, performing again the step of acquiring a cell image of the blood specimen by the cell image analysis apparatus.

11. The method according to claim 1, wherein the method further comprises:
displaying the number of target cells in the blood sample to be tested by the cell image analysis apparatus;
or
transmitting the number of target cells in the blood sample to be tested by the cell image analysis apparatus to other devices for display; and wherein the other devices comprise at least one of a blood analyzer, a blood smear preparation apparatus or a terminal device.

12. A cell image analysis apparatus, comprising: an imaging apparatus, a specimen moving apparatus and a processor;
   wherein the imaging apparatus comprises a camera and a lens group, and is configured to photograph a cell image of a blood specimen, wherein the blood specimen is derived from a blood sample to be tested;
   the specimen moving apparatus is configured to move the blood specimen relative to the imaging apparatus, so that the imaging apparatus is capable of photographing a specific region of the blood specimen; and
   the processor is configured to acquire the cell image, and automatically identify a number of target cells and a number of reference cells in the cell image; and the processor is further configured to acquire a number of reference cells in the blood sample to be tested from a blood analyzer; and the processor is further configured to calculate a number of target cells in the blood sample to be tested based on the number of target cells and the number of reference cells in the cell image and the number of reference cells in the blood sample to be tested.

13. The cell image analysis apparatus according to claim 12, wherein after the processor automatically identifies the number of target cells and the number of reference cells in the cell image, the processor is configured to:
   acquire the number of reference cells in the blood sample to be tested, and calculate the number of target cells in the blood sample to be tested based on the number of target cells and the number of reference cells in the cell image and the number of reference cells in the blood sample to be tested, when the number of reference cells in the cell image is greater than or equal to a first threshold;
   or
   acquire again a cell image of the blood specimen, when the number of reference cells is less than the first threshold.

14. The cell image analysis apparatus according to claim 12, wherein after the processor automatically identifies the number of target cells and the number of reference cells in the cell image, the processor is configured to:
   determine whether a sum of the numbers of reference cells in all cell images of the blood specimen acquired in history is greater than or equal to a second threshold;
   when the sum of the numbers of reference cells in all cell images of the blood specimen acquired in history is greater than or equal to the second threshold, acquire the number of reference cells in the blood sample to be tested, and calculate the number of target cells in the blood sample to be tested based on the sum of the numbers of reference cells in all cell images of the blood specimen, a sum of the numbers of target cells in all cell images of the blood specimen, and the number of reference cells in the blood sample to be tested;
   or
   when the sum of the numbers of reference cells in all cell images of the blood specimen acquired in history is less than the second threshold, acquire again a cell image of the blood specimen.

15. The cell image analysis apparatus according to claim 12, wherein the cell image analysis apparatus further comprises a display apparatus configured to display at least the number of target cells in the blood sample to be tested;
   or
   wherein the processor controls a communication apparatus to transmit the number of target cells in the blood sample to be tested to other devices for display; and
   wherein the other devices comprise at least one of a blood analyzer, a blood smear preparation apparatus or a terminal device.

16. A specimen analysis system, comprising: a cell image analysis apparatus, a blood smear preparation apparatus and a blood analyzer,
   wherein the cell image analysis apparatus comprises an imaging apparatus, a specimen moving apparatus and a processor;
      the imaging apparatus comprises a camera and a lens group, and is configured to photograph a cell image of a blood specimen prepared by the blood smear preparation apparatus; wherein the blood specimen is derived from a blood sample to be tested;
      the specimen moving apparatus is configured to move the blood specimen relative to the imaging apparatus, so that the imaging apparatus is capable of photographing a specific region of the blood specimen; and
      the processor is configured to acquire the cell image, and automatically identify a number of target cells and a number of reference cells in the cell image; and the processor is further configured to acquire the number of reference cells in the blood sample to be tested from the blood analyzer; and the processor is further configured to calculate a number of target cells in the blood sample to be tested based on the number of target cells and the number of reference cells in the cell image and the number of reference cells in the blood sample to be tested;
   wherein the blood smear preparation apparatus is configured to prepare a blood smear of the blood sample to be tested; and wherein the blood smear is used as the blood specimen to be photographed by the imaging apparatus; and
   wherein the blood analyzer is configured to detect the number of reference cells in the blood sample to be tested.

17. The system according to claim 16, wherein the system further comprises a control apparatus that is connected to the blood analyzer, the blood smear preparation apparatus and the cell image analysis apparatus, respectively; and wherein the control apparatus is configured to control a transport device to transport the blood sample to be tested from the blood analyzer to the blood smear preparation apparatus, and is further configured to control the transport device to transport the blood smear prepared by the blood smear preparation apparatus to the cell image analysis apparatus.

18. The system according to claim 16, wherein the blood analyzer is further configured to detect a number of target cells in the blood sample to be tested, independent of the cell image analysis apparatus; and
   wherein the system further comprises a display apparatus, and the display apparatus is configured to display at least one of the number of target cells in the blood sample to be tested calculated by the cell image analysis apparatus, or the number of target cells in the blood sample to be tested detected by the blood analyzer.

19. The system according to claim 18, wherein after the processor automatically identifies the number of target cells and the number of reference cells in the cell image, the processor is further configured to:

determine whether a sum of the numbers of reference cells in all cell images of the blood specimen acquired in history is greater than or equal to a second threshold;

when the sum of the numbers of reference cells in all cell images of the blood specimen acquired in history is greater than or equal to the second threshold, acquire the number of reference cells in the blood sample to be tested, and calculate the number of target cells in the blood sample to be tested based on the sum of the numbers of reference cells in all cell images of the blood specimen, a sum of the numbers of target cells in all cell images of the blood specimen, and the number of reference cells in the blood sample to be tested;

or when the sum of the numbers of reference cells in all cell images of the blood specimen acquired in history is less than the second threshold, acquire again a cell image of the blood specimen.

20. The system according to claim 19, wherein the display apparatus is configured to display the number of target cells in the blood sample to be tested detected by the blood analyzer, when the number of reference cells in all cell images of the blood specimen acquired by the processor of the cell image analysis apparatus is less than the second threshold.

* * * * *